US007585969B2

(12) United States Patent
Stoffel et al.

(10) Patent No.: US 7,585,969 B2
(45) Date of Patent: Sep. 8, 2009

(54) MICRORNA AND METHODS FOR INHIBITING SAME

(75) Inventors: Markus Stoffel, Zurich (CH); Matthew N. Poy, New York, NY (US); Thomas H. Tuschl, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 12/045,484

(22) Filed: Mar. 10, 2008

(65) Prior Publication Data

US 2009/0043082 A1 Feb. 12, 2009

Related U.S. Application Data

(62) Division of application No. 10/824,633, filed on Apr. 13, 2004, now Pat. No. 7,365,058.

(51) Int. Cl.
*C07H 21/04* (2006.01)
*C07H 21/02* (2006.01)
*A61K 48/00* (2006.01)

(52) U.S. Cl. .................. 536/24.5; 514/44; 536/23.1; 536/24.31; 536/24.33

(58) Field of Classification Search ........................ None
See application file for complete search history.

(56) References Cited

U.S. PATENT DOCUMENTS

| 7,217,807 | B2 | 5/2007 | Bentwich |
| 2003/0108923 | A1 | 6/2003 | Tuschl et al. |
| 2006/0166910 | A1 | 7/2006 | Tuschl et al. |
| 2006/0257851 | A1 | 11/2006 | Bentwich |
| 2007/0039072 | A1 | 2/2007 | Khvorova et al. |
| 2007/0042381 | A1 | 2/2007 | Bentwich et al. |
| 2008/0188428 | A1 | 8/2008 | Bentwich |

FOREIGN PATENT DOCUMENTS

| WO | WO03029459 | A2 | 4/2003 |
| WO | WO2004007718 | A2 | 1/2004 |
| WO | WO2004044123 | A2 | 5/2004 |
| WO | WO2004048511 | A2 | 6/2004 |

OTHER PUBLICATIONS

Amarzguioui, Mohammed, et al., "Tolerance for mutations and chemical modifications in a siRNA", Nucleic Acids Research 2003, 31(2):589-595.
Bartel, David P., "MicroRNAs: Genomics, Biogenesis, Mechanism, and Function", Cell 2004, 116:281-297.
Beigelman, Leonid, et al., "Chemical Modification of Hammerhead Ribozymes", The Journal of Biological Chemistry 1995, 270(43):25702-25708.
Elbashir, Sayda M., et al., "Duplexes of 21-nucleotide RNAs mediate RNA interference in cultured mammalian cells", Nature 2001, 411:494-498.

Holen, Torgeir, et al., "Positional effects of short interfering RNAs targeting the human coagulation trigger Tissue Factor", Nucleic Acids Research 2002, 30(8):1757-1766.
Holen, Torgeir, et al., "Similar behaviour of single-strand and double-strand siRNAs suggests they act through a common RNAi pathway", Nucleic Acids Research 2003, 31(9):2401-2407.
Howard, Ken, "Unlocking the money-making potential of RNAi", Nature Biotechnology 2003, 21(12):1441-1446.
Kurreck, Jens, "Antisense technologies Improvement through novel chemical modifications", Eur. J. Biochem. 2003, 270:1628-1644.
Meister, Gunter, et al., "Sequence-specific inhibition of microRNA- and siRNA-induced RNA silencing", RNA 2004, 10:544-550.
Nelson, Peter, et al., "The microRNA world: small is mighty", Trends in Biochemical Sciences 2003, 28(10):534-540.
Database EMBL (Online), *Homo sapiens* Genomic Sequence Surrounding NotI site, clone NR3-B07C, XP002451811 retrieved from EBI accession No. EMBL: AJ332626: $^{21}/_{22}$ residues match SEQ ID No. 1; Oct. 2001, abstract.
Database EMBL (Online), "NISC_js08a05.w1 Soares NMBP1 Mus Musculus cDNA clone Image: 4314537 5', mRNA sequence", XP002451882 retrieved from EBI accession No. EMBL: CB057718; $^{22}/_{22}$ residues match SEQ ID No. 3; Jan. 2003, abstract.
Database EMBL (Online), CH4#001_G02T7 Canine Heart Normalized CDNA Library in pBluescript Canis familaris CDNA clone CH4#001_G02 5', mRNA sequence. XP002451883 retrieved from EBI accession No. EMBL: BU751380: $^{22}/_{22}$ residues match SEQ ID No. 4; Oct. 2002, abstract.
Avavin et al., "The Small RNA Profile During Drosophila Melanogaster Development", Developmental Cell, vol. 5, p. 337-350 (2003).
Beigelman et al., "Chemical Modification of Hammerhead Ribozymes", The Journal of Biological Chemistry, vol. 270, No. 43, p. 25702-25708 (1995).
Liang et al., "Inhibitor RNA Blocks the Protein Translation Mediated by Hepatitis C Virus Internal Ribosome Entry Site in Vivo", World J. Gastroenterol, 10(5), p. 664-667 (2004).
Berezikov et al., "Phylogenetic Shadowing and Computational Identification of Human MicroRNA Genes", Cell, vol. 120, pp. 21-24 (2005).
Seitz, et al., "A Large Imprinted MicroRNA Gene Cluster at the Mouse Elkl-Gtl2 Domain", Genome Research, pp. 2. 1-8 (2004).
Xie et al., "Systematic Discovery of Regulatory Motifs in Human Promoters and 3' UTR's by Comparison of Several Mammals", Nature, pp. 1-8 (2005).
Analysis and accompanying remarks by Rosetta Genomics of the sequences presented in Table A2 of the specification of the instant application (Jun. 28, 2007).
Table of information provided by Rosetta regarding the applications submitted in IDS dated Jul. 12, 2007 (Jun. 28, 2007).
Analysis and accompanying remarks by Rosetta Genomics of the sequences presented in Table A2 of the specification of the instant application (Jun. 28, 2007).
Table of information provided by Rosetta regarding the applications submitted in IDS dated Jul. 12, 2007 (Jun. 28, 2007).

(Continued)

*Primary Examiner*—Amy Bowman
(74) *Attorney, Agent, or Firm*—Hoffmann & Baron, LLP

(57) ABSTRACT

The invention relates to isolated DNA or RNA molecules comprising at least ten contiguous bases having a sequence in a pancreatic islet microRNA. In another embodiment, the invention relates to isolated single stranded pancreatic islet microRNA molecules or anti-pancreatic islet microRNA molecules.

34 Claims, 11 Drawing Sheets

OTHER PUBLICATIONS

Analysis by Rosetta of the sequences of Table A2 compared to those disclosed in Rosetta's patent applications (Jun. 28, 2007).

AC146999, Murphy et al. Oct. 31, 2003, p. 1-67.

Murphy et al., "Coding Potential of Laboratory and Clinical Strains of Human Cytomegalovirus", PNAS, vol. 100, No. 25, p. 14976-14981 (2003).

Taliansky et al., "An Umbraviral Protein, Involved in Long-Distance RNA Movement, Binds Viral RNA and Forms Unique, Protective Ribonucleoprotin Complexes", Journal of Virology, vol. 77, No. 5, p. 3031-3040 (2003).

Paddison et al., "Short Hairpin RNAs (shRNAs) Induce Sequence-Specific Silencing in Mammalian Cells", Genes & Development, 16:948-958 (2002).

Wiebusch et al., "Inhibition of Human Cytomegalovirus Replication by Small Interfering RNAs", Journal of General Virology, 85, p. 179-184 (2004).

Vanitharani et al., "Short Interfering RNA-Mediated Interference of Gene Expression and Viral DNA Accumulation in Cultured Plant Cells", PNAS, vol. 100, No. 16, p. 9632-9636 (2003).

Pfitzner et al., "Isolation and Characterization of cDNA Clones Corresponding to Transcripts from the BamHI H and F Regions of the Epstein-Barr Virus Genome", Journal of Virology, vol. 61, No. 9, p. 2902-2909 (1987).

Pfeffer et al., "Indentification of Virus-Encoded microRNAs", Science, vol. 304, p. 734-736 (2004).

Zeng, et al., "MicroRNAs and Small Interfering RNAs Can Inhibit mRNA Expression by Similar Mechanisms", PNAS, vol. 100, No. 17, p. 9779-9784 (2003).

EMBL Database Accession No. AJ 332626 created Oct. 1, 2001.

EMBL Database Accession No. BU 751380 created Oct. 17, 2002.

EMBL Database Accession No. CB 057718 created Jan. 18, 2003.

Figure 2A

```
C  -     A       CCU   C      C  GAC
 CC CGCG CGAGCC    CG ACAAA CG    C
 GG GUGC GCUCGG    GC UGUUU GC    U      (SEQ. ID. NO. 31)
C  A   -          CUU  U      U  GAG
```

Mtpn wildtype 3'UTR (SEQ. ID. NO. 69)
miR-375 (SEQ. ID. NO. 1)

Mtpn mutant 3'UTR (SEQ. ID. NO. 70)
miR-375 (SEQ. ID. NO. 1)

```
                          SEQUENCE LISTING

<160> NUMBER OF SEQ ID NOS: 70

<210> SEQ ID NO 1
    <211> LENGTH: 22
    <212> TYPE: RNA
    <213> ORGANISM: Homo sapiens

<400> SEQUENCE: 1
uuuguucguu cggcucgcgu ga                                              22

<210> SEQ ID NO 2
    <211> LENGTH: 21
    <212> TYPE: RNA
    <213> ORGANISM: Homo sapiens

<400> SEQUENCE: 2
aucauagagg aaaauccacg u                                               21

<210> SEQ ID NO 3
    <211> LENGTH: 22
    <212> TYPE: RNA
    <213> ORGANISM: Homo sapiens

<400> SEQUENCE: 3
aucacacaaa ggcaacuuuu gu                                              22

<210> SEQ ID NO 4
    <211> LENGTH: 22
    <212> TYPE: RNA
    <213> ORGANISM: Homo sapiens

<400> SEQUENCE: 4
cuccugacuc cagguccugu gu                                              22

<210> SEQ ID NO 5
    <211> LENGTH: 19
    <212> TYPE: RNA
    <213> ORGANISM: Homo sapiens

<400> SEQUENCE: 5
ugguagacua uggaacgua                                                  19

<210> SEQ ID NO 6
    <211> LENGTH: 19
    <212> TYPE: RNA
    <213> ORGANISM: Homo sapiens
```

-continued

```
<400> SEQUENCE: 6
ugguugacca uagaacaug                                                19

<210> SEQ ID NO 7
<211> LENGTH: 22
<212> TYPE: RNA
<213> ORGANISM: Homo sapiens

<400> SEQUENCE: 7
uauacaaggg caagcucucu gu                                            22

<210> SEQ ID NO 8
<211> LENGTH: 22
<212> TYPE: RNA
<213> ORGANISM: Homo sapiens

<400> SEQUENCE: 8
gaaguuguuc gugguggauu cg                                            22

<210> SEQ ID NO 9
<211> LENGTH: 22
<212> TYPE: RNA
<213> ORGANISM: Homo sapiens

<400> SEQUENCE: 9
agaucagaag gugacugugg cu                                            22

<210> SEQ ID NO 10
<211> LENGTH: 20
<212> TYPE: RNA
<213> ORGANISM: Homo sapiens

<400> SEQUENCE: 10
auuccuagaa auuguucaua                                               20

<210> SEQ ID NO 11
<211> LENGTH: 22
<212> TYPE: RNA
<213> ORGANISM: Mouse

<400> SEQUENCE: 11
uuuguucguu cggcucgcgu ga                                            22

<210> SEQ ID NO 12
<211> LENGTH: 21
<212> TYPE: RNA
<213> ORGANISM: Mouse

<400> SEQUENCE: 12
aucguagagg aaaauccacg u                                             21

<210> SEQ ID NO 13
<211> LENGTH: 22
<212> TYPE: RNA
<213> ORGANISM: Mouse

<400> SEQUENCE: 13
aucacacaaa ggcaacuuuu gu                                            22

<210> SEQ ID NO 14
<211> LENGTH: 22
<212> TYPE: RNA
<213> ORGANISM: Mouse
```

-continued

```
<400> SEQUENCE: 14
cuccugacuc cagguccugu gu                                              22

<210> SEQ ID NO 15
<211> LENGTH: 19
<212> TYPE: RNA
<213> ORGANISM: Mouse

<400> SEQUENCE: 15
ugguagacua uggaacgua                                                  19

<210> SEQ ID NO 16
<211> LENGTH: 19
<212> TYPE: RNA
<213> ORGANISM: Mouse

<400> SEQUENCE: 16
ugguugacca uagaacaug                                                  19

<210> SEQ ID NO 17
<211> LENGTH: 22
<212> TYPE: RNA
<213> ORGANISM: Mouse

<400> SEQUENCE: 17
uauacaaggg caagcucucu gu                                              22

<210> SEQ ID NO 18
<211> LENGTH: 22
<212> TYPE: RNA
<213> ORGANISM: Mouse

<400> SEQUENCE: 18
gaaguuguuc gugguggauu cg                                              22

<210> SEQ ID NO 19
<211> LENGTH: 22
<212> TYPE: RNA
<213> ORGANISM: Mouse

<400> SEQUENCE: 19
agaucagaag gugacugugg cu                                              22

<210> SEQ ID NO 20
<211> LENGTH: 20
<212> TYPE: RNA
<213> ORGANISM: Mouse

<400> SEQUENCE: 20 auccuagaa auuguucaca                                                  20

<210> SEQ ID NO 21
<211> LENGTH: 64
<212> TYPE: RNA
<213> ORGANISM: Homo sapiens

<400> SEQUENCE: 21
ccccgcgacg agccccucgc acaaaccgga ccugagcguu uuguucguuc ggcucgcgug     60
aggc                                                                  64

<210> SEQ ID NO 22
```

```
<211> LENGTH: 68
<212> TYPE: RNA
<213> ORGANISM: Homo sapiens

<400> SEQUENCE: 22
uaaaagguag auucuccuuc uaugaguaca uuauuuauga uuaaucauag aggaaaaucc    60
acguuuuc                                                            68

<210> SEQ ID NO 23
<211> LENGTH: 69
<212> TYPE: RNA
<213> ORGANISM: Homo sapiens

<400> SEQUENCE: 23
uugagcagag guugcccuug gugaauucgc uuuauuuaug uugaaucaca caaaggcaac    60
uuuuguuug                                                           69

<210> SEQ ID NO 24
<211> LENGTH: 66
<212> TYPE: RNA
<213> ORGANISM: Homo sapiens

<400> SEQUENCE: 24
ggggcuccug acuccagguc cuguguguua ccucgaaaua gcacuggacu uggagucaga    60
aggccu                                                              66

<210> SEQ ID NO 25
<211> LENGTH: 67
<212> TYPE: RNA
<213> ORGANISM: Homo sapiens

<400> SEQUENCE: 25
agagauggua gacuauggaa cguaggcguu augauuucug accauguaa caugguccac     60 uaacucu                                                             67

<210> SEQ ID NO 26
<211> LENGTH: 61
<212> TYPE: RNA
<213> ORGANISM: Homo sapiens

<400> SEQUENCE: 26
aagaugguug accauagaac augcgcuauc ucugucgu auguaauaug guccacaucu      60
u                                                                   61

<210> SEQ ID NO 27
<211> LENGTH: 75
<212> TYPE: RNA
<213> ORGANISM: Homo sapiens

<400> SEQUENCE: 27
uacuuaaagc gagguugccc uuuguauauu cgguuuauug acauggaaua ucaagggca     60 agcucucugu gagua                                                    75

<210> SEQ ID NO 28
<211> LENGTH: 76
<212> TYPE: RNA
<213> ORGANISM: Homo sapiens

<400> SEQUENCE: 28
uacuugaaga gaaguuguuc gugguggauu cgcuuuacuu augacgaauc auucacggac    60
```
aacacuuuuu ucagua                                              76

<210> SEQ ID NO 29
<211> LENGTH: 73
<212> TYPE: RNA
<213> ORGANISM: Homo sapiens

<400> SEQUENCE: 29
cuccucagau cagaagguga uuguggcuuu ggguggauau uaaucagcca cagcacugcc    60
uggucagaaa gag                                                 73

<210> SEQ ID NO 30
<211> LENGTH: 88
<212> TYPE: RNA
<213> ORGANISM: Homo sapiens

<400> SEQUENCE: 30
uguuaaauca ggaauuuuaa acaauuccua gacaauaugu auaauguuca uaagucauuc    60
cuagaaauug uucauaaugc cuguaaca                                 88

<210> SEQ ID NO 31
<211> LENGTH: 64
<212> TYPE: RNA
<213> ORGANISM: Mouse

<400> SEQUENCE: 31
ccccgcgacg agccccucgc acaaaccgga ccugagcguu uguucguuc ggcucgcgug     60 aggc                                                           64

<210> SEQ ID NO 32
<211> LENGTH: 68
<212> TYPE: RNA
<213> ORGANISM: Mouse

<400> SEQUENCE: 32
uaaaagguag auucuccuuc uaugaguaca auauuaauga cuaaucguag aggaaaaucc    60
acguuuuc                                                       68

<210> SEQ ID NO 33
<211> LENGTH: 68
<212> TYPE: RNA
<213> ORGANISM: Mouse

<400> SEQUENCE: 33
ugagcagagg uugcccuugg ugaauucgcu uuauugaugu ugaaucacac aaaggcaacu    60
uuuguuug                                                       68

<210> SEQ ID NO 34
<211> LENGTH: 66
<212> TYPE: RNA
<213> ORGANISM: Mouse

<400> SEQUENCE: 34
ggggcuccug acuccagguc cuguguguua ccucgaaaua gcacuggacu uggagucaga    60
aggccu                                                         66

<210> SEQ ID NO 35
<211> LENGTH: 66
<212> TYPE: RNA

```
<213> ORGANISM: Mouse

<400> SEQUENCE: 35
agagauggua gacuauggaa cguaggcguu auguuuuuga ccuauguaac augguccacu    60
aacucu                                                              66

<210> SEQ ID NO 36
<211> LENGTH: 61
<212> TYPE: RNA
<213> ORGANISM: Mouse

<400> SEQUENCE: 36
aagaugguug accauagaac augcgcuacu ucugugucgu auguaguaug guccacaucu    60
u                                                                   61

<210> SEQ ID NO 37
<211> LENGTH: 75
<212> TYPE: RNA
<213> ORGANISM: Mouse

<400> SEQUENCE: 37
uacuuaaagc gagguugccc uuuguauauu cgguuuauug acauggaaua acaagggca     60 agcucucugu gagua                                                    75

<210> SEQ ID NO 38
<211> LENGTH: 76
<212> TYPE: RNA
<213> ORGANISM: Mouse

<400> SEQUENCE: 38
uacuugaaga gaaguuguuc gugguggauu cgcuuuacuu gugacgaauc auucacggac    60
aacacuuuuu ucagua                                                   76

<210> SEQ ID NO 39
<211> LENGTH: 70
<212> TYPE: RNA
<213> ORGANISM: Mouse

<400> SEQUENCE: 39
cucagaucag aaggugacug uggcuuuggg uggauauuaa ucagccacag cacugccugg    60
ucagaaagag                                                          70

<210> SEQ ID NO 40
<211> LENGTH: 88
<212> TYPE: RNA
<213> ORGANISM: Mouse

<400> SEQUENCE: 40
uguuaaauca ggaauuguaa acaauuccua ggcaaugugu auaauguugg uaagcauuc     60 cuagaaauug uucacaaugc cguaaaca                                      88

<210> SEQ ID NO 41
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 41
ucacgcgagc cgaacgaaca aa                                            22
```

<210> SEQ ID NO 42
<211> LENGTH: 21
<212> TYPE: RNA
<213> ORGANISM: Artificial sequence
<220> FEATURE:
<223> OTHER INFORMATION: anti-pancreatic islet microRNA molecule

<400> SEQUENCE: 42
acguggauuu uccucuauga u                                        21

<210> SEQ ID NO 43
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 43
acaaaaguug ccuuugugug au                                       22

<210> SEQ ID NO 44
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 44
acacaggacc uggagucagg ag                                       22

<210> SEQ ID NO 45
<211> LENGTH: 19
<212> TYPE: RNA
<213> ORGANISM: Artificial sequence
<220> FEATURE:
<223> OTHER INFORMATION: anti-pancreatic islet microRNA molecule

<400> SEQUENCE: 45
uacguuccau agucuacca                                           19

<210> SEQ ID NO 46
<211> LENGTH: 19
<212> TYPE: RNA
<213> ORGANISM: Artificial sequence
<220> FEATURE:
<223> OTHER INFORMATION: anti-pancreatic islet microRNA molecule

<400> SEQUENCE: 46
cauguucuau ggucaacca                                           19

<210> SEQ ID NO 47
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 47
acagagagcu ugcccuugua ua                                       22

<210> SEQ ID NO 48
<211> LENGTH: 22
<212> TYPE: RNA
<213> ORGANISM: Artificial sequence
<220> FEATURE:

```
<223> OTHER INFORMATION: anti-pancreatic islet microRNA molecule

<400> SEQUENCE: 48
cgaauccacc acgaacaacu uc                                              22

<210> SEQ ID NO 49
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 49
agccacaauc accuucugau cu                                              22

<210> SEQ ID NO 50
<211> LENGTH: 20
<212> TYPE: RNA
<213> ORGANISM: Artificial sequence
<220> FEATURE:
<223> OTHER INFORMATION: anti-pancreatic islet microRNA molecule

<400> SEQUENCE: 50
uaugaacaau uucuaggaau                                                 20

<210> SEQ ID NO 51
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 51
ucacgcgagc cgaacgaaca aa                                              22

<210> SEQ ID NO 52
<211> LENGTH: 21
<212> TYPE: RNA
<213> ORGANISM: Artificial sequence
<220> FEATURE:
<223> OTHER INFORMATION: anti-pancreatic islet microRNA sequence

<400> SEQUENCE: 52
acguggauuu uccucuacga u                                               21

<210> SEQ ID NO 53
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 53
acaaaaguug ccuuugugug au                                              22

<210> SEQ ID NO 54
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 54
acacaggacc uggagucagg ag                                              22
```

```
<210> SEQ ID NO 55
<211> LENGTH: 19
<212> TYPE: RNA
<213> ORGANISM: Artificial sequence
<220> FEATURE:
<223> OTHER INFORMATION: anti-pancreatic islet microRNa molecule

<400> SEQUENCE: 55
uacguuccau agucuacca                                                    19

<210> SEQ ID NO 56
<211> LENGTH: 19
<212> TYPE: RNA
<213> ORGANISM: Artificial sequence
<220> FEATURE:
<223> OTHER INFORMATION: anti-pancreatic islet microRNA molecule

<400> SEQUENCE: 56
cauguucuau ggucaacca                                                    19

<210> SEQ ID NO 57
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 57
acagagagcu ugcccuugua ua                                                22

<210> SEQ ID NO 58
<211> LENGTH: 22
<212> TYPE: RNA
<213> ORGANISM: Artificial sequence
<220> FEATURE:
<223> OTHER INFORMATION: anti-pancreatic islet microRNA sequence

<400> SEQUENCE: 58
cgaauccacc acgaacaacu uc                                                22

<210> SEQ ID NO 59
<211> LENGTH: 22
<212> TYPE: RNA
<213> ORGANISM: Artificial sequence
<220> FEATURE:
<223> OTHER INFORMATION: anti-pancreatic islet microRNA molecule

<400> SEQUENCE: 59
agccacaguc accuucugau cu                                                22

<210> SEQ ID NO 60
<211> LENGTH: 20
<212> TYPE: RNA
<213> ORGANISM: Artificial sequence
<220> FEATURE:
<223> OTHER INFORMATION: anti-pancreatic microRNA molecule

<400> SEQUENCE: 60
ugugaacaau uucuaggaau                                                   20

<210> SEQ ID NO 61
<211> LENGTH: 25
<212> TYPE: DNA
<213> ORGANISM: Artificial sequence
<220> FEATURE:
<223> OTHER INFORMATION: primer
```

-continued

<400> SEQUENCE: 61
tccatcattt catatgcact gtatc                                              25

<210> SEQ ID NO 62
<211> LENGTH: 25
<212> TYPE: DNA
<213> ORGANISM: Artificial sequence
<220> FEATURE:
<223> OTHER INFORMATION: primer

<400> SEQUENCE: 62
tcatatcgtt aaggacgtct ggaaa                                              25

<210> SEQ ID NO 63
<211> LENGTH: 44
<212> TYPE: DNA
<213> ORGANISM: Artificial sequence
<220> FEATURE:
<223> OTHER INFORMATION: primer

<400> SEQUENCE: 63
aagtttcgtg ttgcaagccc ccctggaata aacttgaatt gtgc                         44

<210> SEQ ID NO 64
<211> LENGTH: 44
<212> TYPE: DNA
<213> ORGANISM: Artificial sequence
<220> FEATURE:
<223> OTHER INFORMATION: primer

<400> SEQUENCE: 64
gcacaattca gtttattcc aggggggctt gcaacacgaa actt                          44

<210> SEQ ID NO 65
<211> LENGTH: 25
<212> TYPE: DNA
<213> ORGANISM: Artificial sequence
<220> FEATURE:
<223> OTHER INFORMATION: primer

<400> SEQUENCE: 65
gtgggccctg aaaaacggag acttg                                              25

<210> SEQ ID NO 66
<211> LENGTH: 25
<212> TYPE: DNA
<213> ORGANISM: Artificial sequence
<220> FEATURE:
<223> OTHER INFORMATION: primer

<400> SEQUENCE: 66
ccctttgaca gaagcaattt cacgc                                              25

<210> SEQ ID NO 67
<211> LENGTH: 29
<212> TYPE: DNA
<213> ORGANISM: Artificial Sequence
<220> FEATURE:
<223> OTHER INFORMATION: primer

<400> SEQUENCE: 67
ccccaaggct gatgctgaga agccgcccc                                          29

<210> SEQ ID NO 68
<211> LENGTH: 21

```
-continued

<212> TYPE: DNA
<213> ORGANISM: Artificial Sequence
<220> FEATURE:
<223> OTHER INFORMATION: primer

<400> SEQUENCE: 68
gccgcccggc cccgggtctt c                                            21

<210> SEQ ID NO 69
<211> LENGTH: 25
<212> TYPE: RNA
<213> ORGANISM: Mouse

<400> SEQUENCE: 69
guuucguguu gcaagaacaa augga                                        25

<210> SEQ ID NO 70
<211> LENGTH: 25
<212> TYPE: RNA
<213> ORGANISM: Artificial Sequence
<220> FEATURE:
<223> OTHER INFORMATION: Mutant Mtpn target site

<400> SEQUENCE: 70
guuucguguu gcaagccccc cugga                                        25
```

MICRORNA AND METHODS FOR INHIBITING SAME

This application is a divisional of U.S. application Ser. No. 10/824,633 filed Apr. 13, 2004, the entirety of which is incorporated herein by reference.

BACKGROUND OF THE INVENTION

MicroRNAs are typically small RNA molecules of generally about nineteen to twenty-five nucleotides in length. These microRNAs are non-coding RNAs which are cleaved from hairpin precursors. Several microRNAs have been identified in the genomes of a wide range of multicellular life forms.

Many microRNAs are conserved in sequence between distantly related organisms, and exhibit tissue-specific or developmental stage-specific expression. The conservation of the sequence between organisms indicates that microRNAs may play important roles in biological processes.

MicroRNA molecules have been reported to control gene expression in a sequence specific manner in a wide variety of organisms by blocking translation after partially hybridizing to the non-coding 3' region of mRNAs of target genes. The genes targeted by microRNAs largely remain to be characterized.

However, there is growing evidence that microRNAs are implicated in various diseases and illnesses. For instance, drosophilia microRNAs have been shown to target genes involved in apoptosis. Also, B-cell chronic lymphocytic leukemia has been linked to the deletion of two microRNAs.

Pancreatic islet cells (also referred to as islets of Langerhans) are groups of specialized cells that make and secrete hormones. It is reported that there are five types of cells in an islet: alpha, beta, delta, PP and D1 cells.

Some of these cells are said to be involved in the regulation of glucose. For example, alpha cells secrete glucagon which are hormones involved in raising the level of glucose in the blood. Further, beta cells secrete insulin, a hormone that helps the body utilize glucose for energy.

Interference in the regulation of glucose utilization, particularly of the insulin-secreting beta cells, may lead to diseases and illness such as diabetes. Therefore, it is important to elucidate the mechanisms involved in mediating genes which play a role in the regulation of glucose homeostasis. For example, it is not known in the prior art whether microRNAs, if present, mediate glucose utilization.

Thus, there is a need for materials and methods that can help elucidate the function of regulators, such as microRNAs, of pancreatic islet cells.

Further, due to the ability of microRNAs to induce RNA degradation or repress translation of mRNA, which encode important proteins, there is also a need for novel molecules that inhibit pancreatic microRNA-induced cleavage or translation repression of target mRNAs.

SUMMARY OF THE INVENTION

In one embodiment, the present invention relates to isolated DNA or RNA molecules. The molecules comprise at least ten contiguous bases having a sequence in a pancreatic islet microRNA shown in SEQ ID NOs:1-20, except that up to thirty percent of the bases may be wobble bases, and up to 10% of the contiguous bases may be non-complementary.

In another embodiment, the invention relates to modified single stranded pancreatic islet microRNA molecules. The molecules comprise a minimum of ten moieties and a maximum of fifty moieties on a molecular backbone, the molecular backbone comprising backbone units, each moiety comprising a base bonded to a backbone unit wherein at least ten contiguous bases have the same sequence as a contiguous sequence of bases in a pancreatic islet microRNA molecule shown in SEQ ID NOs:1-20, except that up to thirty percent of the bases pairs may be wobble base pairs, and up to 10% of the contiguous bases may be additions, deletions, mismatches, or combinations thereof, no more than fifty percent of the contiguous moieties contain deoxyribonuleotide backbone units, and at least one moiety is not an unmodified deoxyribonucleotide moiety or an unmodified ribonucleotide moiety.

In a further embodiment, the invention relates to isolated single stranded anti-pancreatic islet microRNA molecules. The molecules comprise a minimum of ten moieties and a maximum of fifty moieties on a molecular backbone, the molecular backbone comprising backbone units, each moiety comprising a base bonded to a backbone unit, each base forming a Watson-Crick base pair with a complementary base wherein at least ten contiguous bases have a sequence complementary to a contiguous sequence of bases in any one of the pancreatic islet microRNA molecules shown in SEQ ID NOs; 1-20, except that up to thirty percent of the base pairs may be wobble base pairs, and up to 10% of the contiguous bases may be additions, deletions, mismatches, or combinations thereof, no more than fifty percent of the contiguous moieties contain deoxyribonuleotide backbone units; and the molecule is capable of inhibiting microRNP activity.

In yet another embodiment, the invention relates to a method for inhibiting microRNP activity in a cell. The microRNP comprises a pancreatic islet microRNA molecule. The method comprises introducing into the cell a single-stranded anti-pancreatic islet microRNA molecule, wherein the anti-pancreatic islet microRNA is complementary to the pancreatic islet microRNA molecule.

In yet a further embodiment, the invention relates to a method for treating diabetes in a mammal in need thereof. The method comprises introducing into the mammal an effective amount of an anti-pancreatic islet microRNA molecule having at least ten contiguous bases having a sequence shown in SEQ ID NOs:41 or 51.

In another embodiment, the invention relates to isolated microRNPs comprising an isolated DNA or RNA molecule in accordance with the present invention.

In yet another embodiment, the invention relates to isolate microRNPs comprising an isolated single stranded pancreatic islet microRNA molecule in accordance with the present invention.

DETAILED DESCRIPTION OF THE INVENTION

Pancreatic Islet MicroRNA Molecules

Figure 1:
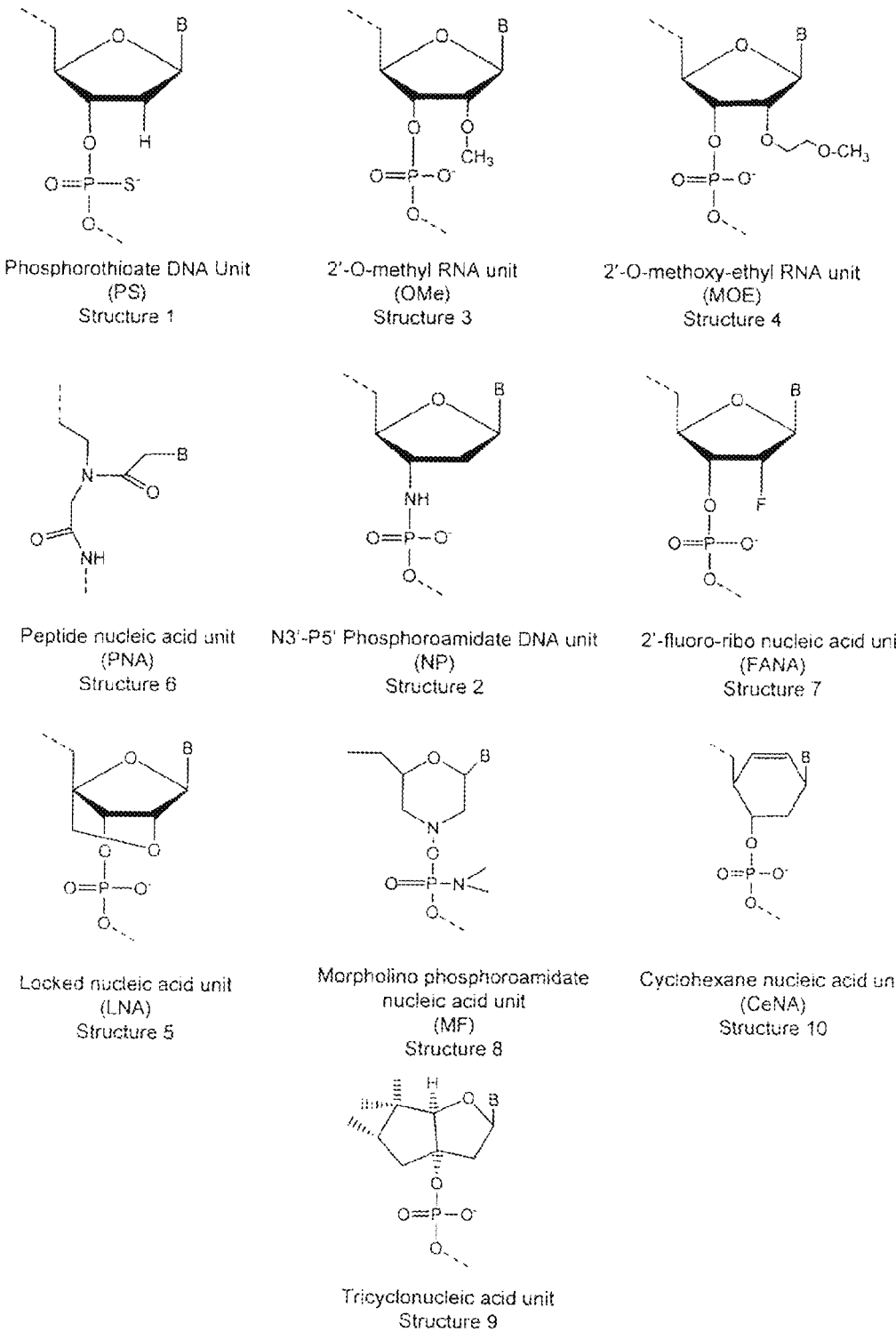
FIG. 1 shows the modified nucleotide units discussed in the specification. B denotes any one of the following nucleic acid bases: adenosine, cytidine, guanosine, thymine, or uridine.

The inventors have discovered novel pancreatic islet microRNA molecules. These molecules have SEQ ID NOs: 1-20. Thus, in one embodiment, the invention relates to an isolated single stranded pancreatic islet microRNA molecule.

MicroRNA molecules are known in the art (see, for example, Bartel, *Cell*, 2004, 116, 281-297 for a review on microRNA molecules). The definitions and characterizations of microRNA molecules in the article by Bartel is hereby incorporated by reference. Such molecules are derived from genomic loci and are produced from specific microRNA genes.

Mature microRNA molecules are processed from precursor transcripts that form local hairpin structures. The hairpin structures are typically cleaved by an enzyme known as Dicer, generating thereby one microRNA duplex. See the above reference by Bartel.

Usually, one of the two strands of a microRNA duplex is packaged in a microRNA ribonucleoprotein complex (microRNP). A microRNP in, for example, humans, also includes the proteins eIF2C2, the helicase Gemin3, and Gemin 4.

In one embodiment, the invention relates to an isolated DNA or RNA molecule comprising at least ten contiguous bases having a sequence shown in SEQ ID NOs:1-20, and equivalents thereof. Preferably, the isolated DNA or RNA molecule comprises at least thirteen, more preferably at least fifteen, and even more preferably at least twenty contiguous bases having a sequence of bases in a pancreatic islet microRNA shown in SEQ ID NOs:1-20.

TABLE A

Pancreatic Islet microRNAs and Hairpin Precursor Sequences. The name of the microRNA with the prefix "hsa" indicates human and the prefix "mmu" indicates a mouse sequence. The pancreatic islet microRNA sequence portion in the hairpin precursor is indicated in bold.

| Name | MicroRNA (5' to 3') | Hairpin Precursor (5' to 3') |
|---|---|---|
| hsa-miR-375 (Isl-1) | UUUGUUCGUUCGG CUCGCGUGA (SEQ ID NO:1) | CCCCGCGACGAGCCCCUCGCACAA ACCGGACCUGAGCGUUUUGUUCGU UCGGCUCGCGUGAGGC (SEQ ID NO:21) |
| hsa-miR-376 (Isl-2) | AUCAUAGAGGAAA AUCCACGU (SEQ ID NO:2) | UAAAAGGUAGAUUCUCCUUCUAUG AGUACAUUAUUUAUGAUUAAUCAU AGAGGAAAAUCCACGUUUUC (SEQ ID NO:22) |
| hsa-miR-377 | AUCACACAAAGGC AACUUUUGU (SEQ ID NO:3) | UUGAGCAGAGGUUGCCCUUGGUGA AUUCGCUUUAUUUAUGUUGAAUCA CACAAAGGCAACUUUUGUUUG (SEQ ID NO:23) |
| hsa-miR-378 | CUCCUGACUCCAG GUCCUGUGU (SEQ ID NO:4) | GGGGCUCCUGACUCCAGGUCCUGU GUGUUACCUCGAAAUAGCACUGGA CUUGGAGUCAGAAGGCCU (SEQ ID NO:24) |
| hsa-miR-379 | UGGUAGACUAUGG AACGUA (SEQ ID NO:5) | AGAGAUGGUAGACUAUGGAACGUA GGCGUUAUGAUUUCUGACCUAUGU AACAUGGUCCACUAACUCU (SEQ ID NO:25) |
| hsa-miR-380 | UGGUUGACCAUAG AACAUG (SEQ ID NO:6) | AAGAUGGUUGACCAUAGAACAUGC GCUAUCUCUGUGUCGUAUGUAAUA UGGUCCACAUCUU (SEQ ID NO:26) |
| hsa-miR-381 | UAUACAAGGGCAA GCUCUCUGU (SEQ ID NO:7) | UACUUAAAGCGAGGUUGCCCUUUG UAUAUUCGGUUUAUUGACAUGGAA UAUACAAGGGCAAGCUCUCUGUGA GUA (SEQ ID NO:27) |
| hsa-miR-382 | GAAGUUGUUCGUG GUGGAUUCG (SEQ ID NO:8) | UACUUGAAGAGAAGUUGUUCGUGG UGGAUUCGCUUUACUUAUGACGAA UCAUUCACGGACAACACUUUUUUC AGUA (SEQ ID NO:28) |
| hsa-miR-383 | AGAUCAGAAGGUG ACUGUGGCU (SEQ ID NO:9) | CUCCUCAGAUCAGAAGGUGAUUGU GGCU**UUGGGUGGAUAUUAAUCAGC CACAGCACUGCCUGGUCAGAAAGA G (SEQ ID NO:29) |
| hsa-miR-384 | AUUCCUAGAAAUU GUUCAUA (SEQ ID NO:10) | UGUUAAAUCAGGAAUUUUAAACAA UUCCUAGACAAUAUGUAUAAUGUU CAUAAGUCAUUCCUAGAAAUUGUU CAUAAUGCCUGUAACA (SEQ ID NO:30) |
| mmu-miR-375 (Isl-1) | UUUGUUCGUUCGGC UCGCGUGA (SEQ ID NO:11) | CCCCGCGACGAGCCCCUCGCACAA ACCGGACCUGAGCGUUUUGUUCGU UCGGCUCGCGUGAGGC (SEQ ID NO:31) |

TABLE A-continued

Pancreatic Islet microRNAs and Hairpin Precursor Sequences. The name of the microRNA with the prefix "hsa" indicates human and the prefix "mmu" indicates a mouse sequence. The pancreatic islet microRNA sequence portion in the hairpin precursor is indicated in bold.

| Name | MicroRNA (5' to 3') | Hairpin Precursor (5' to 3') |
|---|---|---|
| mmu-miR-376 (Isl-2) | AUCGUAGAGGAAAA UCCACGU (SEQ ID NO:12) | UAAAAGGUAGAUUCUCCUUCUAUG AGUACAAUAUUAAUGACUAAUCGU AGAGGAAAAUCCACGUUUUC (SEQ ID NO:32) |
| mmu-miR-377 | AUCACACAAAGGCA ACUUUUGU (SEQ ID NO:13) | UGAGCAGAGGUUGCCCUUGGUGAA UUCGCUUUAUUGAUGUUGAAUCAC ACAAAGGCAACUUUUGUUUG (SEQ ID NO:33) |
| mmu-miR-378 | CUCCUGACUCCAGG UCCUGUGU (SEQ ID NO:14) | GGGGCUCCUGACUCCAGGUCCUGU GUGUUACCUCGAAAUAGCACUGGA CUUGGAGUCAGAAGGCCU (SEQ ID NO:34) |
| mmu-miR-379 | UGGUAGACUAUGGA ACGUA (SEQ ID NO:15) | AGAGAUGGUAGACUAUGGAACGUA GGCGUUAUGUUUUUGACCUAUGUA ACAUGGUCCACUAACUCU (SEQ ID NO:35) |
| mmu-miR-380 | UGGUUGACCAUAGA ACAUG (SEQ ID NO:16) | AAGAUGGUUGACCAUAGAACAUGC GCUACUUCUGUGUCGUAUGUAGUA UGGUCCACAUCUU (SEQ ID NO:36) |
| mmu-miR-381 | UAUACAAGGGCAAG CUCUCUGU (SEQ ID NO:17) | UACUUAAAGCGAGGUUGCCCUUUG UAUAUUCGGUUUAUUGACAUGGAA UAUACAAGGGCAAGCUCUCUGUGA GUA (SEQ ID NO:37) |
| mmu-miR-382 | GAAGUUGUUCGUGG UGGAUUCG (SEQ ID NO:18) | UACUUGAAGAGAAGUUGUUCGUGG UGGAUUCGCUUUACUUGUGACGAA UCAUUCACGGACAACACUUUUUUC AGUA (SEQ ID NO:38) |
| mmu-miR-383 | AGAUCAGAAGGUGA CUGUGGCU (SEQ ID NO:19) | CUCAGAUCAGAAGGUGACUGUGGC UUUGGGUGGAUAUUAAUCAGCCAC AGCACUGCCUGGUCAGAAAGAG (SEQ ID NO:39) |
| mmu-miR-384 | AUUCCUAGAAAUUG UUCACA (SEQ ID NO:20) | UGUUAAAUCAGGAAUUGUAAACAA UUCCUAGGCAAUGUGUAUAAUGUU GGUAAGUCAUUCCUAGAAAUUGUU CACAAUGCCUGUAACA (SEQ ID NO:40) |

In this specification, a base refers to any one of the nucleotide bases normally found in naturally occurring DNA or RNA. The bases can be purines or pyrimidines. Examples of purine bases include adenine (A) and guanine (G). Examples of pyrimidine bases include thymine (T), cytosine (C) and uracil (U). The adenine can be replaced with 2,6-diaminopurine.

Sequences of unmodified nucleic acid molecules disclosed in this specification are shown having uracil bases. Uracil bases occur in unmodified RNA molecules. The invention also includes unmodified DNA molecules. The sequence of bases of the unmodified DNA molecule is the same as the unmodified RNA molecule, except that in the unmodified DNA molecule, the uracil bases are replaced with thymine bases.

Each base in the sequence can form a Watson-Crick base pair with a complementary base. Watson-Crick base pairs as used herein refer to the hydrogen bonding interaction between, for example, the following bases: adenine and thymine (A-T); adenine and uracil (A-U); and cytosine and guanine (C-G).

Equivalents refer to molecules wherein up to thirty percent of the at least ten contiguous bases are wobble bases, and up to ten percent, and preferably up to five percent of the contiguous bases are non-complementary.

As used herein, wobble base refer to either: 1) substitution of a cytosine with a uracil, or 2) the substitution of an adenine with a guanine, in the sequence of the molecule. These wobble base substitutions are generally referred to as UG or GU wobbles. Table B shows the number of contiguous bases and the maximum number of wobble bases in the molecule.

TABLE B

Number of contiguous Bases and Maximum Number of Wobble Bases

| | No. of Contiguous Bases | | | | | | |
|---|---|---|---|---|---|---|---|
| | 10 | 11 | 12 | 13 | 14 | 15 | 16 |
| Max. No. of Wobble Base Pairs | 3 | 3 | 3 | 3 | 4 | 4 | 4 |

| | No. of Contiguous Bases | | | | | | |
|---|---|---|---|---|---|---|---|
| | 17 | 18 | 19 | 20 | 21 | 22 | 23 |
| Max. No. of Wobble Base Pairs | 5 | 5 | 5 | 6 | 6 | 6 | 6 |

The term "non-complementary" as used herein refers to additions, deletions, mismatches or combinations thereof. Additions refer to the insertion in the contiguous sequence of any base described above. Deletions refer to the removal of any moiety present in the contiguous sequence. Mismatches refer to the substitution of one of the bases in the contiguous sequence with a different base.

The additions, deletions or mismatches can occur anywhere in the contiguous sequence, for example, at either end of the contiguous sequence or within the contiguous sequence of the molecule. Typically, the additions, deletions or mismatches occur at the end of the contiguous if the contiguous sequence is relatively short, such as, for example, from about ten to about fifteen bases in length. If the contiguous sequence is relatively long, such as, for example, a minimum of sixteen contiguous sequences, the additions, deletions, or mismatches may occur anywhere in the contiguous sequence.

For example, none or one of the contiguous bases may be additions, deletions, or mismatches when the number of contiguous bases is ten to nineteen; and a maximum of one or two additions, deletions, or mismatches are permissible when the number of contiguous bases is twenty to twenty-three.

In addition to the at least ten contiguous nucleotides of the pancreatic islet microRNA, the isolated DNA or RNA molecule may also have one or more additional nucleotides. There is no upper limit to the additional number of nucleotides. Typically, no more than about 500 nucleotides, and preferably no more than about 300 nucleotides are added to the at least ten contiguous bases of a pancreatic islet microRNA.

Any nucleotide can be added. The additional nucleotides can comprise any base described above. Thus, for example, the additional nucleotides may be any one or more of A, G, C, T, or U.

In one embodiment, the pancreatic islet microRNA is part of a hairpin precursor sequence or fragment thereof. For example, suitable hairpin precursor sequences are shown in SEQ ID NOs:21-40. The fragment can be any fragment of the hairpin precursor sequence containing at least ten, preferably at least fifteen, more preferably at least twenty nucleotides at the 5' end and/or nucleotides at the 3' end. Preferably the sequence of nucleotides is in the hairpin precursor in which the pancreatic islet microRNA is present.

The pancreatic islet microRNA or haipin precursor can be inserted into a vector, such as, for example, a recombinant vector. Typically, to construct a recombinant vector containing a pancreatic islet microRNA, the hairpin precursor sequence which contains the pancreatic islet microRNA sequence is incorporated into the vector. See for example, Chen et al. *Science* 2004, 303:83-86.

The recombinant vector may be any recombinant vector, such as a plasmid, a cosmid or a phage. Recombinant vectors generally have an origin of replication. The vector may be, for example, a viral vector, such as an adenovirus vector or an adeno-associated virus (AAV) vector. See for example: Ledley 1996, *Pharmaceutical Research* 13:1595-1614 and Verma et al. *Nature* 1997, 387:239-242.

The vector may further include a selectable marker. Suitable selectable markers include a drug resistance marker, such as tetracycline or gentamycin, or a detectable gene marker, such as β-galactosidase or luciferase.

In a preferred embodiment, the isolated DNA or RNA molecule consists essentially of any one of the pancreatic islet microRNA sequences or a hairpin precursor sequence shown in SEQ ID NOs:1-40.

In this specification, "isolated" means that the molecule is essentially free of other nucleic acids. Essentially free from other nucleic acids means that the molecule is at least about 90%, preferably at least about 95% and, more preferably at least about 98% free of other nucleic acids.

Preferably, the molecule is essentially pure, which means that the molecules are free not only of other nucleic acids, but also of other materials used in the synthesis and isolation of the molecule. Materials used in synthesis include, for example, enzymes. Materials used in isolation include, for example, gels, such as SDS-PAGE. The molecule is at least about 90% free, preferably at least about 95% free and, more preferably at least about 98% free of such materials.

The islet cells can be any pancreatic islet cell known to those in the art. Examples of pancreatic islet cells include alpha cells, beta cells, delta cells, PP cells and D1 cells. Preferably, the cells are beta cells.

The sequence of bases in a microRNA or hairpin precursor is highly conserved. Due to the high conservation, the sequence can be from a pancreatic cell of any mammal. Examples of mammals include pet animals, such as dogs and cats, farm animals, such as cows, horses and sheeps, laboratory animals, such as rats, mice and rabbits, and primates, such as monkeys and humans. Preferably, the mammal is human or mouse.

Modified Single Stranded Pancreatic Islet microRNA Molecules

In another embodiment, the invention relates to a modified single stranded pancreatic islet microRNA molecule. The modified single stranded microRNA molecule can be any of the pancreatic microRNA molecules, hairpin precursor molecules, or equivalents thereof described above, except that the modified molecule comprises at least one modified moiety (i.e., at least one moiety is not an unmodified deoxyribonucleotide moiety or ribonucleotide moiety). In this embodiment, the modified pancreatic islet microRNA molecule comprises a minimum number of ten moieties, preferably a minimum of thirteen, more preferably a minimum of fifteen, even more preferably a minimum of eighteen, and most preferably a minimum of twenty-one moieties.

The modified pancreatic islet microRNA molecules comprise a maximum number of fifty modified moieties, preferably a maximum of forty, more preferably a maximum of thirty, even more preferably a maximum of twenty-five, and most preferably a maximum of twenty-three modified moieties. A suitable range of minimum and maximum numbers of modified moieties may be obtained by combining any of the above minima with any of the above maxima.

Each modified moiety comprises a base bonded to a backbone unit. The backbone unit may be any molecular unit that is able to stably bind to a base and to form an oligomeric chain. In this specification, the backbone units of a modified moiety do not include the backbone units commonly found in naturally occurring DNA or RNA molecules.

Such modified pancreatic islet microRNA molecules have increased nuclease resistance. Therefore, the nuclease resistance of the molecule is increased compared to a sequence containing only unmodified ribonucleotide moieties, unmodified deoxyribonucleotide moieties or both. Such modified moieties are well known in the art, and were reviewed, for example, by Kurreck, Eur. J. Biochem. 270, 1628-1644 (2003).

The nuclease resisted can be an exonuclease, an endonuclease, or both. The exonuclease can be a 3'→5' exonuclease or a 5'→3' exonuclease. Examples of 3'→5' human exonuclease include PNPT1, Werner syndrome helicase, RRP40, RRP41, RRP42, RRP45, and RRP46. Examples of 5'→3' exonuclease include XRN2, and FEN1. Examples of endonucleases include Dicer, Drosha, RNase4, Ribonuclease P, Ribonuclease H1, DHP1, ERCC-1 and OGG1. Examples of nucleases which function as both an exonuclease and an endonuclease include APE1 and EXO1.

A modified moiety can occur at any position in the pancreatic islet microRNA molecule. For example, to protect pancreatic islet microRNA molecules against 3'→5' exonucleases, the molecules can have at least one modified moiety at the 3' end of the molecule and preferably at least two modified moieties at the 3' end. If it is desirable to protect the molecule against 5'→3' exonuclease, the pancreatic islet microRNA molecules can have at least one modified moiety and preferably at least two modified moieties at the 5' end of the molecule. The pancreatic islet microRNA molecules can also have at least one and preferably at least two modified moieties between the 5' and 3' end of the molecule to increase resistance of the molecule to endonucleases. Preferably, at least about 10%, more preferably at least about 25%, even more preferably at least about 50%, and further more preferably at least about 75%, and most preferably at least about 95% of the moieties are modified. In one embodiment, all of the moieties are modified (e.g., nuclease resistant).

In one example of a modified pancreatic islet microRNA molecule, the molecule comprises at least one modified deoxyribonucleotide moiety. Suitable modified deoxyribonucleotide moieties are known in the art. Such modified deoxyribonucleotide moieties comprise, for example, phosphorothioate deoxyribose groups as the backbone unit. See structure 1 in FIG. 1. A modified pancreatic islet microRNA molecule comprising phosphorothioate deoxyribonucleotide moieties is generally referred to as phosphorothioate (PS) DNA. See, for example, Eckstein, Antisense Nucleic Acids Drug Dev. 10, 117-121 (2000).

Another suitable example of a modified deoxyribonucleotide moiety is an N'3-N'5 phosphoroamidate deoxyribonucleotide moiety, which comprises an N'3-N'5 phosphoroamidate deoxyribose group as the backbone unit. See structure 2 in FIG. 1. An oligonucleotide molecule comprising phosphoroamidate deoxyribonucleotide moieties is generally referred to as phosphoroamidate (NP) DNA. See, for example, Gryaznov et al., J. Am. Chem. Soc. 116, 3143-3144 (1994).

In another example of a modified pancreatic islet microRNA molecule, the molecule comprises at least one modified ribonucleotide moiety. A suitable example of a modified ribonucleotide moiety is a ribonucleotide moiety that is substituted at the 2' position. The substituents at the 2' position may, for example, be a $C_1$ to $C_4$ alkyl group. The $C_1$ to $C_4$ alkyl group may be saturated or unsaturated, and unbranched or branched. Some examples of $C_1$ to $C_4$ alkyl groups include ethyl, isopropyl, and allyl. The preferred $C_1$ to $C_4$ alkyl group is methyl. See structure 3 in FIG. 1. An oligoribonucleotide molecule comprising ribonucleotide moieties substituted at the 2' position with a $C_1$ to $C_4$ alkyl group is generally referred to as a 2'-O-($C_1$-$C_4$ alkyl) RNA, e.g., 2'-O-methyl RNA (OMe RNA).

Another suitable example of a substituent at the 2' position of a modified ribonucleotide moiety is a $C_1$ to $C_4$ alkoxy-$C_1$ to $C_4$ alkyl group. The $C_1$ to $C_4$ alkoxy (alkyloxy) and $C_1$ to $C_4$ alkyl group may comprise any of the alkyl groups described above. The preferred $C_1$ to $C_4$ alkoxy-$C_1$ to $C_4$ alkyl group is methoxyethyl. See structure 4 in FIG. 1. An oligonucleotide molecule comprising more than one ribonucleotide moiety that is substituted at the 2' position with a $C_1$ to $C_4$ alkoxy-$C_1$ to $C_4$ alkyl group is referred to as a 2'-O-($C_1$ to $C_4$ alkoxy-$C_1$ to $C_4$ alkyl) RNA, e.g., 2'-O-methoxyethyl RNA (MOE RNA).

Another suitable example of a modified ribonucleotide moiety is a ribonucleotide that has a methylene bridge between the 2'-oxygen atom and the 4'-carbon atom. See structure 5 in FIG. 1. An oligoribonucleotide molecule comprising ribonucleotide moieties that has a methylene bridge between the 2'-oxygen atom and the 4'-carbon atom is generally referred to as locked nucleic acid (LNA). See, for example, Kurreck et al., Nucleic Acids Res. 30, 1911-1918 (2002); Elayadi et al., Curr. Opinion Invest. Drugs 2, 558-561 (2001); Ørum et al., Curr. Opinion Mol. Ther. 3, 239-243 (2001); Koshkin et al., Tetrahedron 54, 3607-3630 (1998); Obika et al., Tetrahedron Lett. 39, 5401-5404 (1998). Locked nucleic acids are commercially available from Proligo (Paris, France and Boulder, Colo., USA).

Another suitable example of a modified ribonucleotide moiety is a ribonucleotide that is substituted at the 2' position with fluoro group. Such 2'-fluororibonucleotide moieties are known in the art. Molecules comprising 2'-fluororibonucleotide moieties are generally referred to herein as 2'-fluororibo nucleic acids (FANA). See structure 7 in FIG. 1. Damha et al., J. Am. Chem. Soc. 120, 12976-12977 (1998).

In another example of a modified pancreatic islet microRNA molecule, the molecule comprises at least one modified moiety comprising a base bonded to an amino acid residue as the backbone unit. Modified moieties that have at least one base bonded to an amino acid residue will be referred to herein as peptide nucleic acid (PNA) moieties. Such moieties are nuclease resistance, and are known in the art. Molecules having PNA moieties are generally referred to as peptide nucleic acids. See structure 6 in FIG. 1. Nielson, Methods Enzymol. 313, 156-164 (1999); Elayadi, et al, id.; Braasch et al., Biochemistry 41, 4503-4509 (2002), Nielsen et al., Science 254, 1497-1500 (1991).

The amino acids can be any amino acid, including natural or non-natural amino acids. Naturally occurring amino acids include, for example, the twenty most common amino acids normally found in proteins, i.e., alanine (Ala), arginine (Arg), asparagine (Asn), aspartic acid (Asp), cysteine (Cys), glutamine (Glu), glutamic acid (Glu), glycine (Gly), histidine (His), isoleucine (Ileu), leucine (Leu), lysine (Lys), methionine (Met), phenylalanine (Phe), proline (Pro), serine (Ser), threonine (Thr), tryptophan, (Trp), tyrosine (Tyr), and valine (Val).

The non-natural amino acids may, for example, comprise alkyl, aryl, or alkylaryl groups. Some examples of alkyl amino acids include α-aminobutyric acid, β-aminobutyric acid, γ-aminobutyric acid, δ-aminovaleric acid, and ε-aminocaproic acid. Some examples of aryl amino acids include ortho-, meta, and para-aminobenzoic acid. Some examples of alkylaryl amino acids include ortho-, meta-, and para-aminophenylacetic acid, and γ-phenyl-β-aminobutyric acid.

Non-naturally occurring amino acids also include derivatives of naturally occurring amino acids. The derivative of a naturally occurring amino acid may, for example, include the addition or one or more chemical groups to the naturally occurring amino acid.

For example, one or more chemical groups can be added to one or more of the 2', 3', 4', 5', or 6' position of the aromatic ring of a phenylalanine or tyrosine residue, or the 4', 5', 6', or 7' position of the benzo ring of a tryptophan residue. The group can be any chemical group that can be added to an aromatic ring. Some examples of such groups include hydroxyl, $C_1$-$C_4$ alkoxy, amino, methylamino, dimethylamino, nitro, halo (i.e., fluoro, chloro, bromo, or iodo), or branched or unbranched $C_1$-$C_4$ alkyl, such as methyl, ethyl, n-propyl, isopropyl, butyl, isobutyl, or t-butyl.

Other examples of non-naturally occurring amino acids which are derivatives of naturally occurring amino acids include norvaline (Nva), norleucine (Nle), and hydroxyproline (Hyp).

The amino acids can be identical or different from one another. Bases are attached to the amino acid unit by molecular linkages. Examples of linkages are methylene carbonyl, ethylene carbonyl and ethyl linkages. (Nielsen et al., *Peptide Nucleic Acids-Protocols and Applications,* Horizon Scientific Press, pages 1-19; Nielsen et al., *Science* 254: 1497-1500.) One example of an amino acid residue of a PNA moiety is N-(2-aminoethyl)-glycine.

Figure 5A:
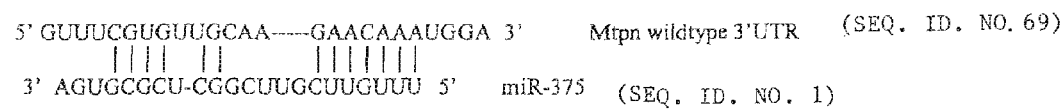
FIG. 5: The miR-375 target site in the 3'UTR of Mtpn is responsible for inhibition of gene expression by miR-375 SEQ. ID. NO. 1. (A) Sequence of the target site in the 3'UTR of myotrophin inserted within the Renilla luciferase 3' UTR. The mutant construct (Mtpn-MUT) SEQ. ID. NO. 70 is identical to the WT construct (Mtpn-WT) SEQ. ID. NO. 69 except for five point mutations (bold) disrupting base-pairing at the 5' end of miR-375. (B) MIN6 cells were transiently transfected with either reporter construct in addition to 2'-O-methyl-oligoribonucleotides complementary to miR-375 (2'-O-methyl-375) or a control 2'-O-oligoribonucleotide (2'-O-methyl-GFP).
Figure 5A:
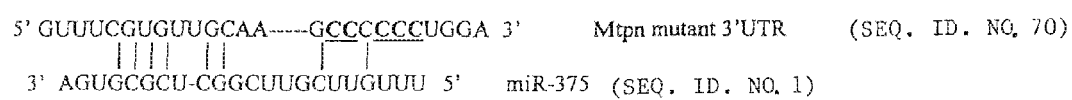
Figure 5B:
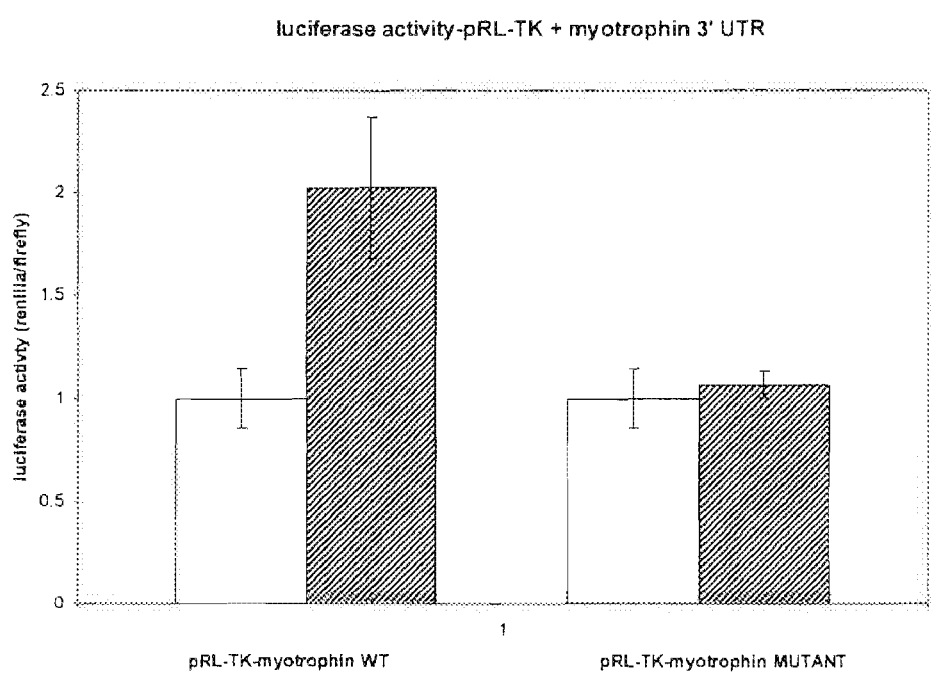

Further examples of PNA moieties include cyclohexyl PNA, retro-inverso PNA, phosphone PNA, propionyl PNA and aminoproline PNA moieties. For a description of these PNA moieties, see FIG. 5 of Nielsen et al., *Peptide Nucleic Acids-Protocols and Applications,* Horizon Scientific Press, pages 1-19. FIG. 5 on page 7 of Nielsen et al. is hereby incorporated by reference.

PNA can be chemically synthesized by methods known in the art, e.g. by modified Fmoc or tBoc peptide synthesis protocols. The PNA has many desirable properties, including high melting temperatures (Tm), high base-pairing specificity with nucleic acid and an uncharged molecular backbone. Additionally, the PNA does not confer RNase H sensitivity on the target RNA, and generally has good metabolic stability.

Peptide nucleic acids are also commercially available from Applied Biosystems (Foster City, Calif., USA).

In another example of a modified pancreatic islet microRNA molecule, the molecule comprises at least one morpholino phosphoroamidate nucleotide moiety. Molecules comprising morpholino phosphoroamidate nucleotide moieties are generally referred to as morpholino (MF) nucleic acids. See structure 8 in FIG. 1. Heasman, Dev. Biol. 243, 209-214 (2002). Morpholino oligonucleotides are commercially available from Gene Tools LLC (Corvallis, Oreg., USA).

In a further example of a modified pancreatic islet microRNA molecule, the molecule comprises at least one cyclohexene nucleotide moiety. Molecules comprising cyclohexene nucleotide moieties are generally referred to as cyclohexene nucleic acids (CeNA). See structure 10 in FIG. 1. Wang et al., J. Am. Chem. Soc. 122, 8595-8602 (2000), Verbeure et al., Nucleic Acids Res. 29, 4941-4947 (2001).

In a final example of a modified pancreatic islet microRNA molecule, the molecule comprises at least one tricyclo nucleotide moiety. Molecules comprising tricyclo nucleotide moieties are generally referred to as tricyclo nucleic acids (tcDNA). See structure 9 in FIG. 1. Steffens et al., J. Am. Chem. Soc. 119, 11548-11549 (1997), Renneberg et al., J. Am. Chem. Soc. 124, 5993-6002 (2002).

Chimeric pancreatic modified islet microRNA molecules containing a mixture of any of the moieties mentioned above are also known, and may be made by methods known, in the art. See, for example, references cited above, and Wang et al, Proc. Natl. Acad. Sci. USA 96, 13989-13994 (1999), Liang et al., Eur. J. Biochem. 269, 5753-5758 (2002), Lok et al., Biochemistry 41, 3457-3467 (2002), and Damha et al., J. Am. Chem. Soc. 120, 12976-12977 (2002).

The modified pancreatic islet microRNA molecules of the invention comprise at least ten, preferably at least thirteen, more preferably at least fifteen, and even more preferably at least twenty contiguous bases having any of the contiguous base sequences of a naturally occurring pancreatic islet microRNA molecule shown in SEQ ID NOs:1-20. In a preferred embodiment, the modified pancreatic islet microRNA molecules comprise the entire sequence of any of the pancreatic islet microRNA molecule shown in SEQ ID NOs:1-20.

Any number of additional moieties, up to a maximum of forty moieties, having any base sequence can be added to the moieties comprising the contiguous base sequence, as long as the total number of moieties in the molecule does not exceed fifty. The additional moieties can be added to the 5' end, the 3' end, or to both ends of the contiguous sequence. The additional moieties can include a sequence of bases at the 5' end and/or a sequence of bases at the 3' end present in the hairpin precursor from which the pancreatic islet microRNA is derived or any fragment thereof. The additional moieties in the molecule, if any, can be any modified or unmodified moiety described above.

The modified pancreatic islet microRNA molecules include equivalents thereof. Equivalents include wobble bases and non-complementary bases as described above.

Further, no more than fifty percent, and preferably no more than thirty percent, of the contiguous moieties contain deoxyribonucleotide backbone units. Table C and D show the maximum number of deoxyribonucleotide backbone units for each number of contiguous bases.

In another embodiment, in addition to the wobble base pairs and non-complementary bases described above, the moiety corresponding to position 11 in a naturally occurring pancreatic islet microRNA sequence can be an addition, deletion or mismatch.

The modified pancreatic islet microRNA molecule is preferably isolated, more preferably purified, as defined above.

TABLE C

Fifty Percent of the Contiguous Moieties containing Deoxyribonucleotide Backbone Units

| | No. of Contiguous Bases | | | | | | |
|---|---|---|---|---|---|---|---|
| | 10 | 11 | 12 | 13 | 14 | 15 | 16 |
| Max. No. of Deoxyribonucleotide Backbone Units | 5 | 5 | 6 | 6 | 7 | 7 | 8 |
| | No. of Contiguous Bases | | | | | | |
| | 17 | 18 | 19 | 20 | 21 | 22 | 23 |
| Max. No. of Deoxyribonucleotide Backbone Units | 8 | 9 | 9 | 10 | 10 | 11 | 11 |

TABLE E

Thirty Percent of the Contiguous Moieties Containing Deoxyribonucleotide Backbone Units

| | No. of Contiguous Bases | | | | | | |
|---|---|---|---|---|---|---|---|
| | 10 | 11 | 12 | 13 | 14 | 15 | 16 |
| Max. No. of Deoxyribonucleotide Backbone Units | 3 | 3 | 3 | 3 | 4 | 4 | 4 |
| | No. of Contiguous Bases | | | | | | |
| | 17 | 18 | 19 | 20 | 21 | 22 | 23 |
| Max. No. of Deoxyribonucleotide Backbone Units | 5 | 5 | 5 | 6 | 6 | 6 | 6 |

In yet another embodiment, caps can be attached to one end, both ends, and/or between the ends of the molecule in order to increase nuclease resistance of the modified pancreatic islet microRNA molecules or unmodified isolated DNA or RNA molecules of the present invention described above to exonucleases. Any cap known to those in the art for increasing nuclease resistance can be employed. Examples of such caps include inverted nucleotide caps and chemical caps.

An inverted nucleotide cap refers to a 3'→5' sequence of nucleic acids attached to the pancreatic islet microRNA molecule at the 5' and/or the 3' end. There is no limit to the maximum number of nucleotides in the inverted cap just as long as it does not interfere with binding of the pancreatic islet microRNA molecule or isolated DNA or RNA molecule to its target mRNA. Any nucleotide can be used in the inverted nucleotide cap. Usually, the nucleotide cap is less than about forty nucleotides in length, preferably less than about thirty nucleotides in length, more preferably less than about twenty nucleotides in length, and even more preferably less than about ten nucleotides in length. Typically, the inverted nucleotide cap is one nucleotide in length. The nucleotide for the inverted cap is generally thymine, but can be any nucleotide such as adenine, guanine, uracil, or cytosine.

Alternatively, a chemical cap can be attached to the 5' end, to the 3' end, to both ends of the molecule, and/or to any moiety(ies) between the 5' end and 3' end of the modified pancreatic islet microRNA molecule or isolated DNA or RNA molecule in order to increase nuclease resistance to exonucleases and/or endonucleases. The chemical cap can be any chemical group known to those in the art for increasing nuclease resistance of nucleic acids. Examples of such chemical caps include hydroxyalkyl or aminoalkyl groups. Hydroxyalkyl groups are sometimes referred to as alkyl glycoyl groups (e.g., ethylene glycol). Aminoalkyl groups are sometimes referred to as amino linkers.

The alkyl chain in the hydroxyalkyl group or aminoalkyl groups can be a straight chain or branched chain. The minimum number of carbon atoms present in the alkyl chain is one, preferably at least two, and more preferably at least about three carbon atoms. The maximum number of carbon atoms present in the alkyl chain is about eighteen, preferably about sixteen, and more preferably about twelve. Typical alkyl groups include methyl, ethyl, and propyl. The alkyl groups can be further substituted with one or more hydroxyl and/or amino groups.

Some examples of amino linkers are shown in Table E. The amino linkers listed in Table E are commercially available from TriLink Biotechnologies, San Diego, Calif.

Isolated MicroRNP

In another aspect, the invention provides an isolated microRNP comprising any of the isolated DNA or RNA molecules described above or modified pancreatic islet microRNA molecules described above.

Anti-Pancreatic Islet MicroRNA Molecules

In another aspect, the invention provides an anti-pancreatic islet microRNA molecule. The anti-pancreatic islet microRNA molecule may be any of the isolated DNA or RNA molecules described above or modified pancreatic islet microRNA molecules described above, except that the sequence of bases of the anti-pancreatic islet microRNA molecule is complementary to the sequence of bases in an isolated DNA or RNA molecule or modified pancreatic islet microRNA molecule.

Examples of sequences of anti-pancreatic islet microRNA molecules are shown in Table F.

TABLE E

Amino Linkers from TriLink Biotechnologies

2'-Deoxycytidine-5-C6 Amino Linker (3' Terminus)
2'-Deoxycytidine-5-C6 Amino Linker (5' or Internal)
3' C3 Amino Linker
3' C6 Amino Linker
3' C7 Amino Linker
5' C12 Amino Linker
5' C3 Amino Linker
5' C6 Amino Linker
C7 Internal Amino Linker
Thymidine-5-C2 Amino Linker (5' or Internal)
Thymidine-5-C6 Amino Linker (3' Terminus)
Thymidine-5-C6 Amino Linker (Internal)

TABLE F

Anti-pancreatic islet microRNA Sequences

| MicroRNA | Anti-microRNA Sequence (5'→3') |
|---|---|
| hsa-miR-375 (Isl-1) | UCACGCGAGCCGAACGAACAAA (SEQ ID NO:41) |
| hsa-miR-376 (Isl-2) | ACGUGGAUUUCCUCUAUGAU (SEQ ID NO:42) |
| hsa-miR-377 | ACAAAAGUUGCCUUUGUGUGAU (SEQ ID NO:43) |

TABLE F-continued

Anti-pancreatic islet microRNA Sequences

| MicroRNA | Anti-microRNA Sequence (5'→3') |
|---|---|
| hsa-miR-378 | ACACAGGACCUGGAGUCAGGAG (SEQ ID NO:44) |
| hsa-miR-379 | UACGUUCCAUAGUCUACCA (SEQ ID NO:45) |
| hsa-miR-380 | CAUGUUCUAUGGUCAACCA (SEQ ID NO:46) |
| hsa-miR-381 | ACAGAGAGCUUGCCCUUGUAUA (SEQ ID NO:47) |
| hsa-miR-382 | CGAAUCCACCACGAACAACUUC (SEQ ID NO:48) |
| hsa-miR-383 | AGCCACAAUCACCUUCUGAUCU (SEQ ID NO:49) |
| hsa-miR-384 | UAUGAACAAUUUCUAGGAAU (SEQ ID NO:50) |
| mmu-miR-375 (Isl-1) | UCACGCGAGCCGAACGAACAAA (SEQ ID NO:51) |
| mmu-miR-376 (Isl-2) | ACGUGGAUUUCCUCUACGAU (SEQ ID NO:52) |
| mmu-miR-377 | ACAAAAGUUGCCUUUGUGUGAU (SEQ ID NO:53) |
| mmu-miR-378 | ACACAGGACCUGGAGUCAGGAG (SEQ ID NO:54) |
| mmu-miR-379 | UACGUUCCAUAGUCUACCA (SEQ ID NO:55) |
| mmu-miR-380 | CAUGUUCUAUGGUCAACCA (SEQ ID NO:56) |
| mmu-miR-381 | ACAGAGAGCUUGCCCUUGUAUA (SEQ ID NO:57) |
| mmu-miR-382 | CGAAUCCACCACGAACAACUUC (SEQ ID NO:58) |
| mmu-miR-383 | AGCCACAGUCACCUUCUGAUCU (SEQ ID NO:59) |
| mmu-miR-384 | UGUGAACAAUUUCUAGGAAU (SEQ ID NO:60) |

The anti-pancreatic islet microRNA molecule can be modified as described above for modified pancreatic islet microRNA molecules. In one embodiment, the contiguous moieties in the anti-pancreatic islet microRNA molecule are complementary to the corresponding pancreatic islet microRNA molecule. The degree of complementarity of the anti-pancreatic islet microRNA molecules are subject to the same restrictions described above for modified pancreatic islet microRNA molecules, including the restriction relating to wobble base pairs, as well as those relating to additions, deletions and mismatches.

In a preferable embodiment, if the anti-micro pancreatic microRNA molecule comprises only unmodified moieties, then the anti-pancreatic islet microRNA molecule comprises at least one base, in the at least ten contiguous bases, which is non-complementary to the pancreatic islet microRNA and/or comprises a chemical cap.

In another preferable embodiment, if the at least ten contiguous bases in an anti-pancreatic islet microRNA molecule is perfectly (i.e., 100%) complementary to a pancreatic islet microRNA molecule, then the anti-pancreatic islet microRNA molecule contains at least one modified moiety in the at least ten contiguous bases and/or comprises a chemical cap.

In yet another embodiment, the moiety in the anti-pancreatic islet microRNA molecule at the position corresponding to position 11 of a naturally occurring pancreatic islet microRNA is non-complementary. The moiety in the anti-pancreatic islet microRNA molecule corresponding to position 11 of a naturally occurring pancreatic islet microRNA can be rendered non-complementary by the introduction of an addition, deletion or mismatch, as described above.

Utility

The pancreatic islet microRNA molecules and anti-pancreatic islet microRNA molecules of the present invention have numerous in vitro, ex vivo, and in vivo applications.

For example, the microRNA molecules and/or anti-microRNA molecules of the present invention can be introduced into a cell to study the function of the microRNA. Any pancreatic islet microRNA molecule and/or anti-pancreatic islet microRNA mentioned above can be introduced into a cell for studying their function.

In one embodiment, a microRNA in a cell is inhibited with a suitable anti-pancreatic islet microRNA molecule. Alternatively, the activity of a pancreatic islet microRNA molecule in a cell can be enhanced by introducing into the cell an additional microRNA molecule. The function of the microRNA can be inferred by observing changes associated with inhibition and/or enhanced activity of the microRNA in the cell.

Thus, in one aspect of the invention, the invention relates to a method for inhibiting microRNP activity in a cell. The microRNP comprises a pancreatic microRNA molecule. Any anti-pancreatic islet microRNA molecule can be used in the method for inhibiting microRNP activity in a cell, as long as the anti-pancreatic islet microRNA molecule is complementary, subject to the restrictions described above, to the pancreatic islet microRNA present in the microRNP.

The anti-pancreatic islet microRNA molecules of the present invention are capable of inhibiting microRNP activity by binding to the pancreatic islet microRNA in the microRNP in a host cell. MicroRNP activity refers to the cleavage or the repression of translation of a target sequence. The target sequence may be any sequence which is partially or perfectly complementary to the sequence of bases in a pancreatic islet microRNA. The target sequence may, for example, be a gene which controls glucose utilization.

For example, pancreatic islet cells can produce a microRNA which is complementary to a gene involved in glucose-induced insulin secretion. The microRNA molecule, which is packaged in a microRNP, will inhibit the beneficial effect of glucose-induced insulin secretion. Accordingly, the introduction of the anti-microRNA molecule inhibits the microRNP activity, and thereby reduces the harm by restoring the function of the gene.

Alternatively, instead of introducing the anti-microRNA molecule mentioned above, additional microRNA molecules can be introduced into the pancreatic islet cell. Accordingly, the gene for glucose-induced insulin secretion will be inhibited, thereby decreasing the ability of the cell to secrete insulin in response to glucose.

The microRNA molecules and/or anti-microRNA molecules can be introduced into a cell by any method known to those skilled in the art. The method for inhibiting microRNP activity in a cell comprises introducing into the cell a single-stranded anti-pancreatic islet microRNA molecule.

For example, the microRNA molecules and/or anti-microRNA molecules can be injected directly into a cell, such as by microinjection. Alternatively, the molecules can be contacted with a cell, preferably aided by a delivery system.

Useful delivery systems include, for example, liposomes and charged lipids. Liposomes typically encapsulate oligonucleotide molecules within their aqueous center. Charged lipids generally form lipid-oligonucleotide molecule complexes as a result of opposing charges.

These liposomes-oligonucleotide molecule complexes or lipid-oligonucleotide molecule complexes are usually internalized in cells by endocytosis. The liposomes or charged lipids generally comprise helper lipids which disrupt the endosomal membrane and release the oligonucleotide molecules.

Other methods for introducing a microRNA molecule or an anti-microRNA into a cell include use of delivery vehicles, such as dendrimers, biodegradable polymers, polymers of amino acids, polymers of sugars, and oligonucleotide-binding nanoparticles. In addition, pluoronic gel as a depot reservoir can be used to deliver the anti-microRNA oligonucleotide molecules over a prolonged period. The above methods are described in, for example, Hughes et al., Drug Discovery Today 6, 303-315 (2001); Liang et al. Eur. J. Biochem. 269 5753-5758 (2002); and Becker et al., In *Antisense Technology in the Central Nervous System* (Leslie, R. A., Hunter, A. J. & Robertson, H. A., eds), pp. 147-157, Oxford University Press.

Targeting of a microRNA molecule or an anti-microRNA molecule to a particular cell can be performed by any method known to those skilled in the art. For example, the microRNA molecule or anti-microRNA molecule can be conjugated to an antibody or ligand specifically recognized by receptors on the cell. For example, the ligand can be GLP-1 (glucagons-like peptide) which binds GLP-receptors expressed on pancreatic beta-cells. Alternatively, an antibody to GLP-1 can be employed.

In another embodiment, the invention provides a method for treating diabetes in a mammal in need thereof. The method comprises introducing into the mammal an effective amount of an anti-pancreatic islet microRNA molecule having at least ten contiguous bases having a sequence shown in SEQ ID NOs:41 or 51. The effective amount is determined during pre-clinical trials and clinical trials by methods familiar to physicians and clinicians.

The anti-pancreatic islet microRNA molecules can be introduced into the mammal by any method known to those in the art. For example, the above described methods for introducing the anti-pancreatic islet molecules into a cell can also be used for introducing the molecules into a mammal.

The molecules can be administered to a mammal by any method known to those skilled in the art. Some examples of suitable modes of administration include oral and systemic administration. Systemic administration can be enteral or parenteral. Liquid or solid (e.g., tablets, gelatin capsules) formulations can be employed.

Parenteral administration of the molecules include, for example intravenous, intramuscular, and subcutaneous injections. For instance, a molecule may be administered to a mammal by sustained release, as is known in the art. Sustained release administration is a method of drug delivery to achieve a certain level of the drug over a particular period of time.

Other routes of administration include oral, topical, intrabronchial, or intranasal administration. For oral administration, liquid or solid formulations may be used. Some examples of formulations suitable for oral administration include tablets, gelatin capsules, pills, troches, elixirs, suspensions, syrups, and wafers. Intrabronchial administration can include an inhaler spray. For intranasal administration, administration of a molecule of the present invention can be accomplished by a nebulizer or liquid mist.

The molecules of the present invention can be in a suitable pharmaceutical carrier. In this specification, a pharmaceutical carrier is considered to be synonymous with a vehicle or an excipient as is understood by practitioners in the art. Examples of carriers include starch, milk, sugar, certain types of clay, gelatin, stearic acid or salts thereof, magnesium or calcium stearate, talc, vegetable fats or oils, gums and glycols.

The pharmaceutical carrier may also comprise one or more of the following: a stabilizer, a surfactant, preferably a nonionic surfactant, and optionally a salt and/or a buffering agent.

The stabilizer may, for example, be an amino acid, such as for instance, glycine; or an oligosaccharide, such as for example, sucrose, tetralose, lactose or a dextran. Alternatively, the stabilizer may be a sugar alcohol, such as for instance, mannitol; or a combination thereof. Preferably the stabilizer or combination of stabilizers constitutes from about 0.1% to about 10% weight for weight of the molecules.

The surfactant is preferably a nonionic surfactant, such as a polysorbate. Some examples of suitable surfactants include Tween 20, Tween 80; a polyethylene glycol or a polyoxyethylene polyoxypropylene glycol, such as Pluronic F-68 at from about 0.001% (w/v) to about 10% (w/v).

The salt or buffering agent may be any salt or buffering agent, such as for example sodium chloride, or sodium/potassium phosphate, respectively. Preferably, the buffering agent maintains the pH of the molecules of the present invention in the range of about 5.5 to about 7.5. The salt and/or buffering agent is also useful to maintain the osmolality at a level suitable for administration to a mammal. Preferably the salt or buffering agent is present at a roughly isotonic concentration of about 150 mM to about 300 mM.

The pharmaceutical carrier may additionally contain one or more conventional additives. Some examples of such additives include a solubilizer such as, for example, glycerol; an antioxidant such as for example, benzalkonium chloride (a mixture of quaternary ammonium compounds, known as "quart"), benzyl alcohol, chloretone or chlorobutanol; anaesthetic agent such as for example a morphine derivative; or an isotonic agent etc., such as described above. As a further precaution against oxidation or other spoilage, the molecules may be stored under nitrogen gas in vials sealed with impermeable stoppers.

EXAMPLES

Example 1

Materials and Methods

MicroRNA cloning and Northern blotting analysis: 600 μg of total RNA was isolated from MIN6 cell cultures using TRIZOL reagent (Invitrogen) and miRNA cloning was performed as previously described (Lagos-Quintana, Current Biol.). Antisense probes were designed to complement cloned miRNA sequences and used for Northern blot analysis as previously described (Lagos-Quintana, Current Biol.).

Cell culture: MIN6 cells were cultured with DMEM medium containing 25 mM glucose, 15% fetal bovine serum, and 5.5 μM 2-mercaptoethanol. N2A cells were cultured with DMEM medium containing 25 mM glucose and 10% fetal bovine serum.

Insulin secretion studies: MIN6 cells were cultured in 24-well plates for 2 days and washed with a modified Krebs-Ringer buffer (KRBH) (0.9 mM $CaCl_2$, 2.68 mM KCl, 1.46 mM $KH_2PO_4$, 0.5 mM $MgCl_2.6H_2O$, 135 mM NaCl, 8 mM $Na_2HPO_4 \times 7H_2O$, 20 mM Hepes, and 0.2% BSA) prior to the assay. After a 30 minute pre-incubation with KRBH containing 5.5 mM glucose, cells were rinsed and incubated for 60 minutes in KRBH with either 2.8 mM glucose, 25 mM glucose, 30 mM KCl, 500 mM tolbutamide, or 5 mM methyl pyruvate. The concentration of insulin in the supernatant was measured using RIA (Linco Research).

Generation of recombinant adenovirus: The recombinant adenovirus used to overexpress miR-375 was generated by PCR amplifying the miRNA precursor sequence with primers: 5'-CCCCAAGGCTGATGCTGAGAAGCCGCCCC-3' SEQ. ID. NO. 67 and 5'-GCCGCCCGGCCCCGGGTCTTC-3' SEQ. ID. NO. 68. The fragment was subcloned into pcDNA 3 (Invitrogen), excised with HindIII and XbaI and inserted into a Ad5CMV-K NpA shuttle vector. Amplification of the adenovirus was performed by Viraquest Inc. (North Liberty, Iowa). Ad-GFP (ViraQuest Inc.) does not contain a transgene and was used as control.

Electrophysiology and $Ca^{2+}$-measurements: Measurements of exocytosis and inward $Ca^{2+}$-currents were conducted on single dispersed B-cells≧24 h after infection with control-GFP- or miRNA208-GFP-containing adenoviruses using the standard whole-cell configuration of the patch-clamp technique. Exocytosis was detected as changes in cell capacitance, using the software-based lock-in implementation of Pulse (Heka Electronics. Lamprecht/Pfalz, Germany). The applied sine wave had a frequency of 500 Hz and a peak amplitude of 20 mV. The $Ca^{2+}$-currents were measured after leak currents and capacitive transients had been removed digitally using a −p/4 protcol. The extracellular solution contained (in mM) 118 NaCl, 20 mM tetraethylammonium-chloride (TEA-Cl), 5.6 KCl, 2.6 $CaCl_2$, 1.2 $MgCl_2$, 5 HEPES (pH=7.4) with 5 glucose. In the experiments in which exocytosis was triggered by voltage-clamp depolarizations, the intracellular solution consisted of (in mM) 125 Cs-glutamate, 10 CsCl, 10 NaCl, 1 $MgCl_2$, 5 HEPES (pH=7.15 with CsOH), 0.05 EGTA, 3 Mg-ATP and 0.1 cyclic AMP. In one series of experiments exocytosis was evoked dialyzing the cell interior with a medium composed of (in mM) 125 Cs-glutamate, 10 KCl, 10 NaCl, 1 $MgCl_2$, 3 Mg-ATP, 0.1 cAMP, 10 HEPES, 10 EGTA and 9 $CaCl_2$. The free $Ca^{2+}$-concentration of this solution was estimated to be 1.5 μM. The experiments were conducted on functionally identified α- and β-cells. The identity of the cells was established as described previously.

The free intracellular $Ca^{2+}$-concentration ($[Ca^{2+}]_i$) was measured by dual-excitation wavelength spectrofluorimetry as described elsewhere. Transfected islets were loaded with 3 μM fura-2 in the presence of 0.007% w/v pluronic acid (Molecular probes) for 40 min at 37° C. The dye was excited at 350 nm and 365 nm. The latter wavelength was used instead of 380 nm in order to avoid excitation of GFP. Emitted light was collected at 510 nm. During the experiments the islets were held in place by a holding pipette and superfused continuously with a medium containing (in mM) 140 NaCl, 3.6 KCl, 2 $NaHCO_3$, 0.5 $NaH_2PO_4$, 0.5 $MgSO_4$, 2.6 $CaCl_2$, 5 HEPES (pH=7.4 mM with NaOH) and 5 mM glucose. The glucose concentration was increased to 15 mM and the sulphonylurea tolbutamide added at a concentration of 0.1 mM as indicated. When the islets were depolarized with high extracellular $K^+$ (30 mM KCl added), the concentration of NaCl was correspondingly decreased to maintain iso-osmolarity. All electrophysiological experiments and $Ca^{2+}$-measurements were carried out at 32-34° C.

The infection of the islets and loading with the $Ca^{2+}$-indicator were evaluated using confocal microscopy and using fluo-3 instead of fura-2. Excitation of both eGFP and fluo-3 was performed using the 488 nm line of a Zeiss LSM510 microscope (Carl Zeiss, Jena, Germany). Emitted light was separated by using the META facility of the confocal microscope and visualized using a 40× water objective.

Assay of luciferase activity: The wildtype mouse myotrophin 3' UTR target site was PCR amplified using the following primers: 5' TCCATCATTTCATATGCACTGTATC 3' SEQ. ID. NO. 61 and 5' TCATATCGTTAAGGACGTCTG-GAAA 3' SEQ. ID. NO. 62 and subcloned into pCR 2.1 TOPO (Invitrogen). The fragment was removed with SpeI and XbaI and subsequently subcloned into the XbaI site immediately downstream of stop codon in pRL-TK (Promega). This construct was used to generate the mutant mouse myotrophin plasmid using primers: 5' AAGTTTCGT-GTTGCAAGCCCCCCTGGAATAAACTTGAATTGTGC 3' SEQ. ID. NO. 63 and 5' GCACAATTCAAGTTTATTCCA GGGGGGCTTGCAACACGAAACTT 3' SEQ. ID. NO. 64 according to protocol (Stratagene); bold and underline indicate mutated nucleotides. MIN6 cells were cultured in 24 well plates for 2 days and transfected with both 0.4 µg of the pRL-TK reporter vector coding for Rr-luc and 0.1 µg of the pGL3 control vector coding for Pp-luc (Promega). Cells were harvested 30-36 hours post-transfection and assayed.

Identification of miR-375 targets: To identify targets of miR-375 we used a recently developed algorithm [N. Rajewsky and N. D. Socci, Developmental Biology 267, 529-535 (2004)]. The algorithm consists of two steps: (a) the search for a GC-rich string of consecutive complementary bases ("nucleus") between the microRNA and the putative target sequence in the 3' UTRs of mRNAs and (b) in silico evaluation of the free energy of the predicted microRNA:mRNA duplex. We applied the algorithm to the Refseq data set. The 3' UTRs were extracted from the Refseq annotation. This dataset comprises 18199 human and 13371 mouse 3' UTRs with a length of at least 30 nucleotides. We further used the Jackson lab orthology table of 9612 human/mouse orthologs to construct a set of orthologous 3' UTRs. Following [Lewis BP, Shih IH, Jones-Rhoades MW, Bartel DP, Burge CB, Prediction of mammalian microRNA targets. Cell 787-98 (2003)] we restricted the position of the nucleus to be within 2 bases from the 5' end of the microRNA. The cutoff for the nucleus score in (a) was set such that that the top 8% of hits were retained. These hits were then scored by their predicted mRNA:miRNA duplex free energy via MFOLD (Zuker, NAR 3406-15, 2003; see Rajewsky and Socci for details).

siRNA and 2'-O-methyl oligoribonucleotides: Synthetic microRNA and siRNAs were synthesized by Dharmacon Research (Lafayette, Colo.). siRNA SMARTPOOLs were designed from the mouse myotrophin (NM_008098) and mouse Vti1A (NM_016862) sequences. All 2'-O-methyl oligoribonucleotides were synthesized as previously described (Meister et al., RNA). All reagents were tranfected into MIN6 cells using Lipofectamine 2000 (Invitrogen) at a 200 nM concentration.

Antibodies: Antibodies for Western blotting were obtained from several different sources: α-myotrophin (donated by Masato Taoka), α-Vti1a (BD Transduction Laboratories), α-p38 MAPK (Cell Signaling), α-MCT8 (donated by Andrew Halestrap), α-TATA box binding protein (donated by R. Roeder).

Northern blotting: Total RNA was extracted using TRI-ZOL reagent (Invitrogen) and loaded onto 15% polyacrylamine or agarose gels. After electrophoresis, RNA was transferred to Hybond membrane (Amersham) and probed. A DNA probe for mouse myotrophin was generated using primers: 5' GTGGGCCCTGAAAAACGGAGACTTG 3' SEQ. ID. NO. 65 and 5° CCCTTTGACAGAAGCAATTTCACGC 3' SEQ. ID. NO. 66.

Example 2

Pancreatic Islet microRNAs

MicroRNAs from MIN6 cells, a glucose responsive murine pancreatic β-cell line were cloned. We obtained a total of 301 microRNAs clones, which contained 55 different microRNAs. Of the 55 different microRNAs, 92% represented previously identified microRNAs and 8% were as-yet unidentified micronAs. Known and novel miRNAs were identified in various genome databases by Blast sequence analysis and confirmed by cross-species homology and their ability to form typical hairpin precursor structures.

Figure 2B:
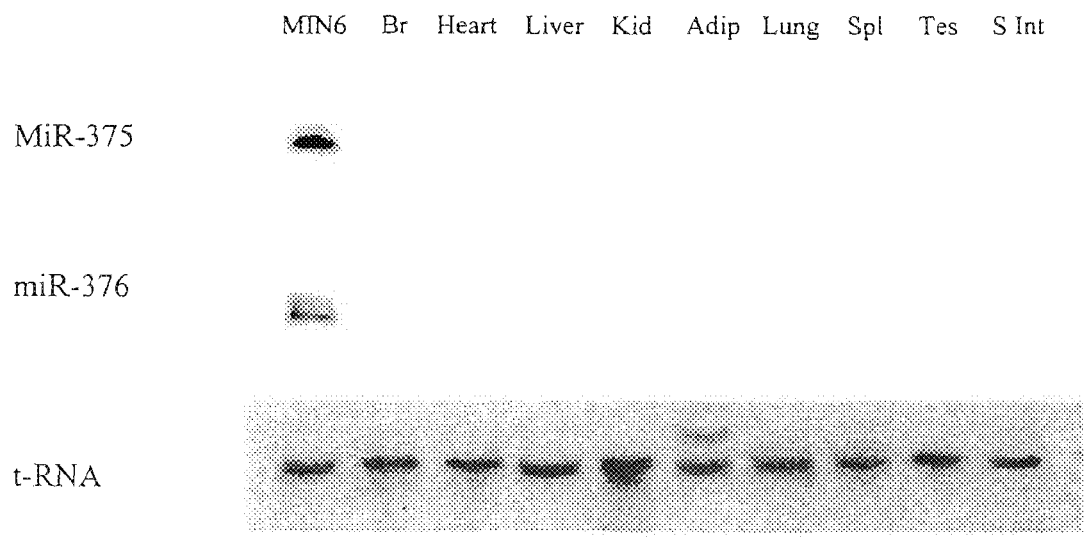
FIG. 2: Predicted precursor structure and tissue expression of mouse miR-375. (A) RNA secondary structure prediction was performed using Mfold version 3.1 SEQ. ID. NO. 31. The miRNA sequence is underlined. There is complete homology between mouse and human sequences. (B) Tissue expression of miR-375 and -376. Total RNA (30 µg) were isolated from mouse tissues for Northern blots and probed for the indicated miRNA. (C) Northern blots of total RNA (10 µg) isolated from purified pancreatic islets, MIN6 cells and total pancreas. High expression levels were detected in mouse pancreatic islets. A tRNA probe was used as a loading control.
Figure 2C:
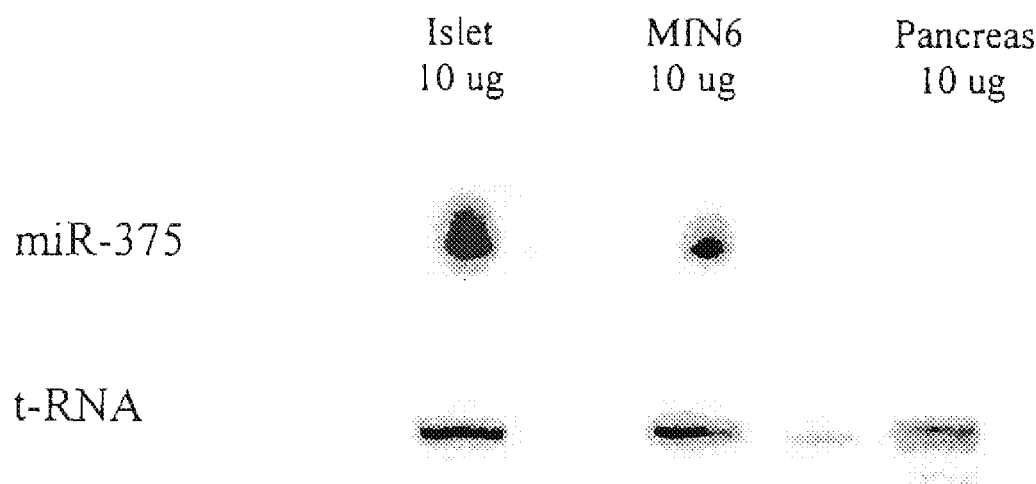

A total of 9 novel microRNAs were identified and a single microRNA (miR-375) represented>50% of all novel clones (FIG. 2a). We next investigated the expression of novel microRNAs by Northern blot analysis. Only microRNAs 375 and 376 could be detected by Northern blot analysis from MIN6 cells and pancreatic islets (FIG. 2b). The expression of both microRNAs was restricted to MIN6 cells and pancreatic islets and not found in other tissues including liver, lung, intestine, brain, kidney and testes (FIG. 2b, c). These data suggested that we had identified novel, pancreatic islet microRNAs.

Example 3

Inhibitory Action of miR-375 on Secretion

To analyze the function of the microRNAs with high expression levels and relative tissue specificity for pancreatic β-cells, we tested the effect of synthetic siRNAs with homologous sequence to microRNAs-375 and -376 on glucose-induced insulin secretion in MIN6 cell following transfection. In addition to the siRNAs, we cotranfected a vector expressing the human growth hormone (hGH) gene under the control of a CMV promoter (CMV-hGH). Exogenously expressed hGH has been previously shown to be targeted to secretory granules of pancreatic b-cell lines and to be co-released with insulin after triggering of exocytosis. This approach allowed us to monitor exocytosis selectively from transiently transfected MIN6 cells (transfection efficiency 20-30%). As positive and negative controls, siRNAs targeting the glucokinase gene (Gck) or apolipoprotein M (apoM), a gene not expressed in pancreatic β-cells, were cotranfected with CMV-hGH into MIN6 cells.

Growth hormone secretion in response to a 25 mM glucose stimulus was significantly decreased in cells transfected with si-Gck and si-375 (FIG. 3). Transfection of synthetic siRNA directed against apoM or siRNAs homologous to several other microRNAs, including miR-376, miR-124,-129,-130, and -210 had no effect on basal or glucose-stimulated insulin secretion (FIG. 3, data not shown).

Figure 3A:
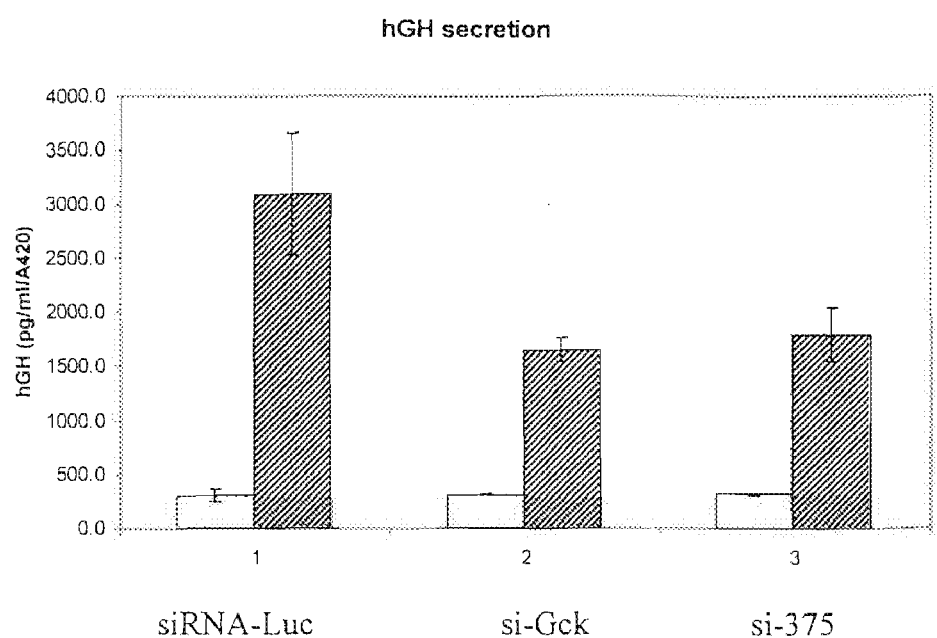
FIG. 3: Inhibitory action of miR-375 on secretion. (A) MIN6 cells were transiently co-transfected with 100 ng of plasmid DNA encoding CMV-hGH and β-gal in addition to synthetic siRNAs with homologous sequence to miRNAs 375, glucokinase or luciferase (si-375, siRNA-Gck and siRNA-luc, respectively) or (B) with 2'-O-methyl-oligoribonucleotides complementary to miR-375 (2'-O-methyl-375) or a control 2'-O- oligoribonucleotide (2'-O-methyl-GFP). After 48 h, the cells were incubated under low (2.8 mM) and stimulatory concentrations of glucose (25 mM). The amount of hGH released under these conditions was measured by ELISA and normalized to β-gal activity. *:P≦0.05, **:P≦0.01).
Figure 3B:
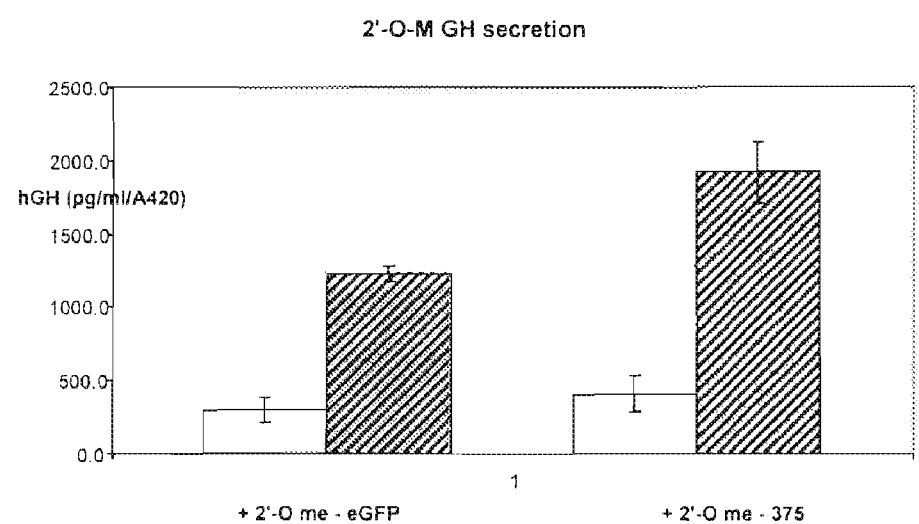

Antisense-based strategies have recently been shown to specifically inhibit miRNA function in cultured cells. We co-transfected nuclease-resistant 2'-O-methyl antisense oligoribonucleotides to miR-375 with vector CMV-hGH and measured insulin secretion in response to stimulation with glucose. We noted an increase in glucose-stimulated insulin secretion of cells transfected with anti-miR-375 compared to a control anti-GFP 2'-O-methyl oligoribonucleotide (FIG. 3b). Together, these data indicated that miR-375 is an inhibitor of insulin secretion.

We next generated a recombinant adenovirus expressing miR-375 by cloning a 123 bp fragment containing the precursor sequence under the control of the CMV5 promoter. HEK cells were infected with a control adenovirus expressing eGFP (Ad-GFP) or increasing concentrations of Ad-375 particles showed a dose dependent increase of miR-375 expression. We also expressed miR-375 in MIN6 cells using adenoviral infections. MIN6 cells expressing miR-375 exhibited a 40% reduction in glucose-induced insulin secretion compared to cells that were infected with a control adenovirus (FIG. 4.). The defect in insulin secretion did not appear to be caused by defective insulin production, since insulin content was equivalent in Ad-375 and Ad-eGFP infected MIN6 cells and pancreatic islets.

Example 4

Intracellular Calcium Signalling and Whole-Cell Calcium Currents

An increase in glycolytic flux and mitochondrial oxidative phosphorylation are required to generate secondary signals for glucose-induced insulin secretion by inducing closure of ATP-sensitive $K^+$ channels (KATP) via an increase in the cytosolic ATP/ADP ratio. This leads to membrane depolarization and influx of $Ca^{++}$ through voltage-dependent $Ca^{++}$ channels. The elevation in $[Ca^{++}]_I$ is a necessary prerequisite for insulin granule exocytosis. Sulphonylurea drugs like glibenclamide stimulate insulin secretion by directly blocking KATP. KCl leads to direct depolarization of pancreatic β-cells and leads to a maximum degranulation of competent insulin granules. We measured insulin secretion in Ad-375 infected MIN6 cells that were stimulated with tolbutamide and KCl. Stimulation of pancreatic β-cells cells with these secretagogues showed impaired insulin secretion in Ad-375 infected cells compared to Ad-eGFP infected cells. Furthermore, Ad-375 expression also impaired insulin secretion in response to GLP-1, a potent glucose-dependent stimulator of insulin secretion through activation of camp, compared to Ad-eGFP infected MIN6 cells. These data suggested that overexpression of miR-375 led to a defect that involves the distal steps of insulin secretion, possibly affecting a rise in cytoplasmic $Ca^{++}$ in pancreatic β-cells or interfering with exocytosis.

To examine whether miR-375 impairs the generation of secondary signals that are required to trigger insulin exocytosis, we measured intracellular $Ca^{++}$ concentrations $[Ca^{2+}]_i$ in islets that were infected with Ad-375 or control Ad-eGFP. Each islet was stimulated by three different stimuli to increase the intracellular $Ca^{2+}$-concentration. Increasing the glucose concentration from 5 mM to 15 mM generated oscillations in the $Ca^{2+}$-concentration in both the control and the Ad-375 expressing islets. Similar oscillations were observed when stimulating with tolbutamide. The resting $[Ca^{2+}]_i$ averaged 0.13±0.01 µM and 0.12±0.01 µM in control and Ad-375 expressing islets, respectively. The time-averaged $[Ca^{2+}]_i$ in the presence of 15 mM glucose amounted to 0.42±0.12 µM in control islets and 0.39±0.05 µM in islets expressing Ad-375. The corresponding values in the presence of tolbutamide were 0.53±0.11 µM in the control islets and 0.55±0.11 µM in the Ad-375-infected islets. Finally, depoalrization with high extracellular $K^+$ increased $[Ca^{2+}]_i$ to the same extent in control and Ad-375-infected islets and the peak $[Ca^{2+}]_i$ averaged 0.85±0.24 µM and 1.01±0.31 µM, respectively (data not shown). Qualitatively similar observations were obtained using the non-ratiometric dye fluo-3 (see above). Moreover, no differences in glucose responsiveness were likewise observed when the measurements were carried out on eGFP-expressing isolated cells, excluding contribution of deeper non-infected cell layers (data not shown). The islet periphery is enriched in non-β-cells. However, the fact that no oscillations were observed at 5 mM glucose and that an elevation to 15mM increased $[Ca^{2+}]_i$ suggests that we had selected a β-cell-rich zone as δ-cells would be active already at the lower concentration and α-cells should be inhibited at the higher concentration.

The characterization of regulated insulin secretion from MIN6 cells and isolated islets indicated that miR-375 expression might affect insulin secretion downstream of $[Ca^{++}]_i$ signaling, possibly at the level of exocytosis. To address this hypothesis, we applied capacitance measurements to functionally-identified β-cells. Exocytosis was elicited by a train of ten 500 ms depolarizations from −70 mV to 0 mV applied at 1 Hz (FIG. 3A). In the β-cells, the train elicited an increase in membrane capacitance of 837±244 fF (n=9) under control conditions. In cells infected with Ad-375, the corresponding increase was limited to 94±27 fF (n=10; P<0.01), a decrease by 85%. Similar results was also obtained once exocytosis instead was induced by a $Ca^{2+}$/EGTA-buffer with a free $Ca^{2+}$-concentration of 1.5 µM (FIG. 2D-E) and in these experiments the rate of capacitance increase was reduced by 63% (P<0.001; n=15-17) in Ad-375-infected cells compared to the control cells.

Example 5

Identification of Target Genes

We applied an algorithm which combines thermodynamics-based modeling of RNA:RNA duplex interactions with comparative sequence analysis to predict microRNA targets conserved across multiple genome. From the compiled list of 64 putative miR-375 target genes, we selected six genes based on their potential role in insulin secretion/islet differentiation for validation studies.

Figures 4A, 4B:
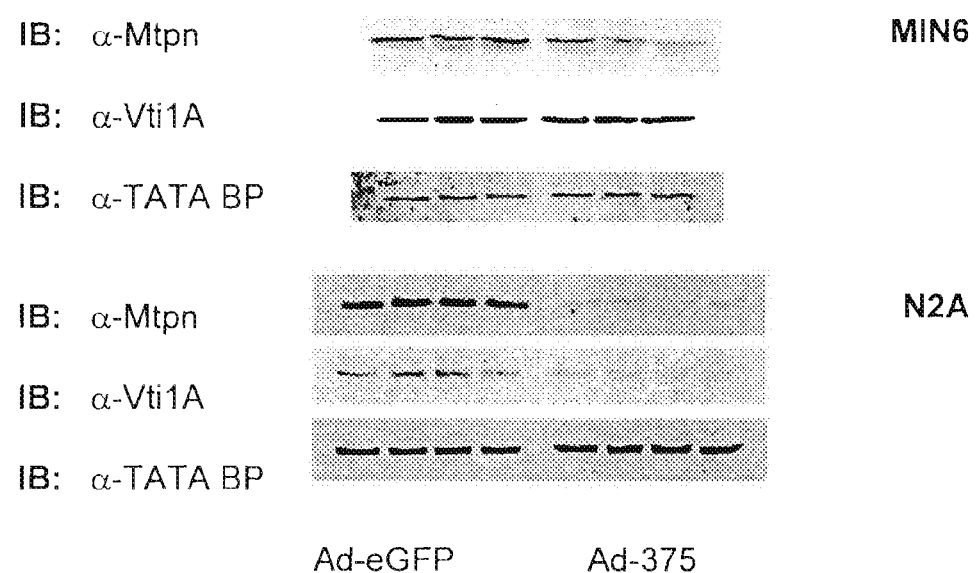
FIG. 4: Identification of target genes of miR-375. (A) MIN6 cells were infected with Ad-miR-375 for 48 h. Following lysis, samples were separated by SDS-PAGE, and immunoblotted with α-Mtpn, α-Vti1a, or a-TATA box binding protein (Tbp)(loading control). (B) Experiment was repeated using N2A cells. (C) MIN6 cells transiently transfected with siRNAs designed against Mtpn (siRNA-Mtpn) or Vti1a (siVti1a) for 48 h and lysed. After analysis by SDS-PAGE, samples were immunoblotted for either Mtpn or Vti1a. (D) MIN6 cells were transiently transfected with si-375, si-Mtpn, or si-Vti1a. After 48 h, the cells were incubated under low (2.8 mM) and stimulatory concentrations of glucose (25 mM). The amount of hGH released under these conditions was measured by ELISA and normalized to β-gal activity. *:P≦0.05, **:P≦0.01).

These genes included the frizzled homolog-4 (Fzd4), vesicle transport through interaction with t-SNAREs yeast homolog 1A (Vti-1a), V-1/myotrophin (V-1/Mtpn), p38 mitogen-activated protein kinase (Mapk11), monocarboxylic acid transporter member 8 (Slc16A2) and the paired box protein Pax-6. The expression of these genes was studied by immunoblotting in MIN6 and N2A cells that were infected with either Ad-375 or Ad-eGFP. Expression of miR-375 in N2A cells, which do not express endogenous miR-375, led to a reduction in expression levels of Mtpn and Vti-1a (FIG. 4A, B).

In contrast, gene expression of Fzd4, Mapk11 and Slc16A2 were equivalent in Ad-375 and Ad-eGFP infected cells. Overexpression of miR-375 in MIN6 cells using recombinant adenovirus Ad-375 also decreased protein levels of Mtpn but had no effect on the expression of Vti-1a, Fzd4, Mapk11 and Slc16A2.

To investigate if the predicted miR-375 target site in the 3' UTR of the Mtpn mRNA was responsible for silencing of Mtpn expression by miR-375, we cloned a 289 nt 3'UTR segment that included the putative 3' UTR target site downstream of a Renilla luciferase ORF (pRL-Mtpn) and co-transfected this reporter vector into MIN6 cells with a control antisense 2'-O-methyl oligoribonucleotides or an miR-375 antisense 2'-O-methyl oligoribonucleotide (2'-O-miR-375). Luciferase activity of cells transfected with the 2'-O-miR-375 was 2~fold increased compared to cells that were co-transfected with control 2'-O-miRNA and pRL-Mtpn. Furthermore, creating point mutations in the core of the miR-375 target site, thereby reducing the complementarity between endogenous miR-375 and the V-1/myotrophin target site, abolished the stimulatory action of 2'-O-miR-375 on luciferase activity (FIG. 5). Therefore, Mtpn is a target of miR-375 in pancreatic β-cells and the repression of Mtpn gene expression is mediated by a single miR-375 target site in the 3' UTR of the Mtpn gene.

Figure 4C:
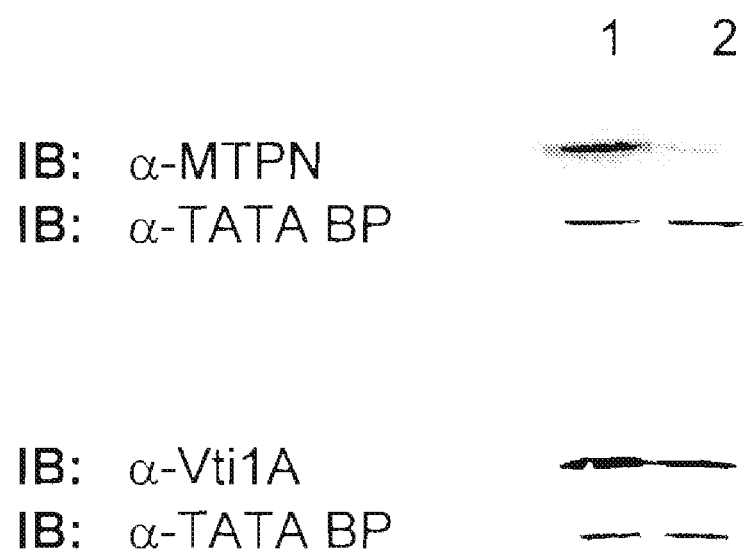
Figure 4D:
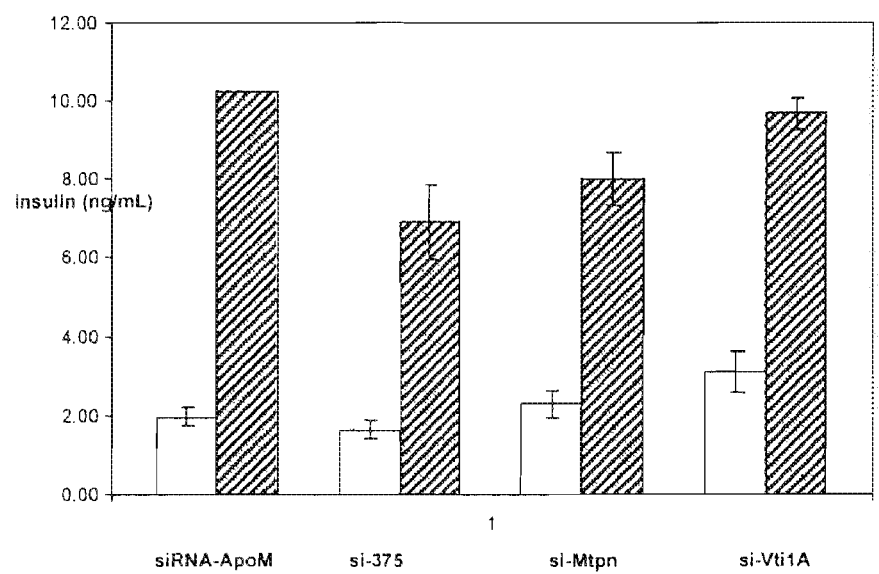

To test if decreased expression of Mtpn in MIN6 cells may contribute to the defect in glucose-induced insulin secretion observed in Ad-375 infected cells, MIN6 cells were transfected with siRNAs targeting apolipoprotein M (control) and Mtpn and protein expression levels were assayed by western blotting. Both siRNAs targeting Mtpn and Vti1 a reduced expression of these genes by >50% (FIG. 4c). The effect of gene silencing of these genes on glucose-induced insulin secretion was studied by co-transfection of the respective siRNA and plasmid pCMV-hGH. Insulin secretion in response to a 25 mM glucose challenge was measured 2 days after transfection. Insulin secretion was reduced ≈30% in cells transfected with siRNA targeting Mtpn compared to cells that were transfected with control siRNA (FIG. 4d). RNA silencing of Vti1a had no effect on glucose-induced insulin secretion.

What is claimed is:

1. An isolated DNA or RNA molecule comprising a maximum of fifty moieties, wherein each moiety comprises a base bonded to a backbone unit, each molecule comprising the sequence of bases identified in SEQ. ID. NO. 1.

2. An isolated DNA or RNA molecule consisting of the sequence of bases in the hairpin precursor of SEQ ID NO: 21.

3. A molecule according to claim 1, wherein at least one of the moieties is a modified deoxyribonucleotide moiety.

4. A molecule according to claim 3 wherein the modified deoxyribonucleotide is a phosphorothioate deoxyribonucleotide moiety.

5. A molecule according to claim 3, wherein the modified deoxyribonucleotide is a N'3-N'5 phosphoroamidate deoxyribonucleotide moiety.

6. A molecule according to claim 1, wherein at least one of the moieties is a modified ribonucleotide moiety.

7. A molecule according to claim 6, wherein the modified ribonucleotide is substituted at the 2' position.

8. A molecule according to claim 7, wherein the substituent at the 2' position is a $C_1$ to $C_4$ alkyl group.

9. A molecule according to claim 8, wherein the alkyl group is methyl.

10. A molecule according to claim 8, wherein the alkyl group is allyl.

11. A molecule according to claim 7, wherein the substituent at the 2' position is a $C_1$ to $C_4$ alkoxy-$C_1$ to $C_4$ alkyl group.

12. A molecule according to claim 11, wherein the $C_1$ to $C_4$ alkoxy-$C_1$ to $C_4$ alkyl group is methoxyethyl.

13. A molecule according to claim 6, wherein the modified ribonucleotide has a methylene bridge between the 2'-oxygen atom and the 4'-carbon atom.

14. A molecule according to claim 1, wherein at least one of the moieties is a peptide nucleic acid moiety.

15. A molecule according to claim 1, wherein at least one of the moieties is a 2'-fluororibonucleotide moiety.

16. A molecule according to claim 1, wherein at least one of the moieties is a morpholino phosphoroamidate nucleotide moiety.

17. A molecule according to claim 1, wherein at least one of the moieties is a tricyclo nucleotide moiety.

18. A molecule according to claim 1, wherein at least one of the moieties is a cyclohexene nucleotide moiety.

19. A molecule according to claim 1, wherein the molecule is a chimeric molecule.

20. A molecule according to claim 1, wherein the molecule comprises at least one modified moiety for increased nuclease resistance.

21. A molecule according to claim 20, wherein the nuclease is an exonuclease.

22. A molecule according to claim 21, wherein the molecule comprises at least one modified moiety at the 5' end.

23. A molecule according to claim 21, wherein the molecule comprises at least two modified moieties at the 5' end.

24. A molecule according to claim 21, wherein the molecule comprises at least one modified moiety at the 3' end.

25. A molecule according to claim 21, wherein the molecule comprises at least two modified moieties at the 3' end.

26. A molecule according to claim 21, wherein the molecule comprises at least one modified moiety at the 5' end and at least one modified moiety at the 3' end.

27. A molecule according to claim 21, wherein the molecule comprises at least two modified moieties at the 5' end and at least two modified moieties at the 3' end.

28. A molecule according to claim 21, wherein the molecule comprises a cap at the 5' end, the 3' end, or both ends of the molecule.

29. A molecule according to claim 28, wherein the molecule comprises a chemical cap.

30. A molecule according to claim 28, wherein the molecule comprises an inverted nucleotide cap.

31. A molecule according to claim 28, wherein the nuclease is an endonuclease.

32. A molecule according to claim 31, wherein the molecule comprises at least one modified moiety between the 5' and 3' end.

33. A molecule according to claim 31, wherein the molecule comprises a chemical cap between the 5' end and 3' end.

34. A molecule according to claim 1, wherein all of the moieties are nuclease resistant.

* * * * *